(12) United States Patent
Bohlmann et al.

(10) Patent No.: US 7,572,794 B2
(45) Date of Patent: Aug. 11, 2009

(54) ANTHRANILAMIDE PYRIDINUREAS AS VASCULAR ENDOTHELIAL GROWTH FACTOR (VEGF) RECEPTOR KINASE INHIBITORS

(75) Inventors: Rolf Bohlmann, Berlin (DE); Martin Haberey, Berlin (DE); Andreas Huth, Berlin (DE); Stuart James Ince, Berlin (DE); Martin Krueger, Berlin (DE); Karl-Heinz Thierauch, Berlin (DE); Holger Hess-Stumpp, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 566 days.

(21) Appl. No.: 11/265,516

(22) Filed: Nov. 3, 2005

(65) Prior Publication Data

US 2006/0264425 A1 Nov. 23, 2006

Related U.S. Application Data

(60) Provisional application No. 60/626,919, filed on Nov. 12, 2004.

(30) Foreign Application Priority Data

Mar. 11, 2004 (EP) .................................. 04090418

(51) Int. Cl.
*A61K 31/535* (2006.01)
*A61K 31/47* (2006.01)
*C07D 413/00* (2006.01)
*C07D 211/80* (2006.01)

(52) U.S. Cl. .................... 514/236.5; 514/311; 514/314; 514/322; 544/116; 544/119; 546/194

(58) Field of Classification Search .............. 546/268.1, 546/290, 304, 314, 329, 194; 514/236.5, 514/311, 314, 322; 544/116, 119
See application file for complete search history.

(56) References Cited

U.S. PATENT DOCUMENTS

| | | | |
|---|---|---|---|
| 3,226,394 | A | 12/1965 | Schippet et al. |
| 4,568,687 | A | 2/1986 | Wright et al. |
| 5,716,993 | A | 2/1998 | Ozaki et al. |
| 6,448,277 | B2 | 9/2002 | Altmann et al. |
| 6,548,548 | B2 | 4/2003 | Campbell et al. |
| 6,818,661 | B2 | 11/2004 | Seidelmann et al. |
| 6,878,720 | B2 | 4/2005 | Altmann et al. |
| 7,002,022 | B2 | 2/2006 | Altmann et al. |
| 7,122,547 | B1 | 10/2006 | Huth et al. |
| 7,148,357 | B2 | 12/2006 | Huth et al. |
| 7,202,260 | B2 | 4/2007 | Huth et al. |
| 7,307,088 | B2 | 12/2007 | Huang et al. |
| 7,429,592 | B2 | 9/2008 | Ernst et al. |
| 2002/0019414 | A1 | 2/2002 | Altmann et al. |
| 2002/0147198 | A1 | 10/2002 | Chen et al. |
| 2003/0134836 | A1 | 7/2003 | Elbaum et al. |
| 2003/0176469 | A1 | 9/2003 | Seidelmann et al. |
| 2003/0225106 | A1 | 12/2003 | Askew et al. |
| 2004/0029880 | A1 | 2/2004 | Krueger et al. |
| 2004/0039019 | A1 | 2/2004 | Huth et al. |
| 2004/0102441 | A1 | 5/2004 | Krueger et al. |
| 2004/0254185 | A1 | 12/2004 | Ernst et al. |
| 2004/0266770 | A1 | 12/2004 | Ernst et al. |
| 2005/0032816 | A1 | 2/2005 | Ernst et al. |
| 2005/0054654 | A1 | 3/2005 | Huth et al. |
| 2005/0261343 | A1 | 11/2005 | Krueger et al. |
| 2006/0116380 | A1 | 6/2006 | Bohlmann et al. |
| 2006/0160861 | A1 | 7/2006 | Bohlmann et al. |
| 2006/0264425 | A1 | 11/2006 | Bohlmann et al. |
| 2007/0015794 | A1 | 1/2007 | Huth et al. |
| 2007/0135489 | A1 | 6/2007 | Huth et al. |

FOREIGN PATENT DOCUMENTS

| | | |
|---|---|---|
| DE | 2652144 A | 5/1978 |
| DE | 3406416 A1 | 8/1984 |
| DE | 19910396 A1 | 9/2000 |
| DE | 10023486 | 3/2002 |
| DE | 10228090 | 1/2004 |
| EP | 0564356 A1 | 10/1993 |
| EP | 0650961 A1 | 5/1995 |
| EP | 06/86625 A1 | 12/1995 |
| JP | 50157383 A | 12/1975 |
| WO | WO 9426260 A1 | 11/1994 |
| WO | WO 96/09294 A | 3/1996 |
| WO | WO 00/27819 | 5/2000 |
| WO | WO 00/27820 | 5/2000 |
| WO | WO 00/39118 A | 7/2000 |
| WO | WO 01/55114 A1 | 8/2001 |

(Continued)

OTHER PUBLICATIONS

Golub et al. Science (1999), vol. 286 521-537.*
Lala et al., Cancer and Metastasis Reviews (1998), 17(1), 91-106.*
"Cancer." Retrieved via Internet Jan. 10, 2008, URL: http://www.nlm.nih.gov/medlineplus/cancer.html.*
"Tautomer." Retrieved via Internet Jan. 10, 2008, URL: http://en.wikipedia.org/wiki/Tautomer.*
"Isomer." Retrieved via Internet Jan. 10, 2008, URL: http://en.wikipedia.org/wiki/Isomer.*
Database Registry (Online) Chemical Abstracts Service, Columbus, Ohio, US.
Augustin et al.: "Antiangiogenic Tumour Therapy: Will it Work?" Elsevier Trends Journal, vol. 19, No. 6, Jun. 1, 1998, pp. 216-222, XP004145666.

(Continued)

*Primary Examiner*—Kamal A Saeed
*Assistant Examiner*—Samantha L Shterengarts
(74) *Attorney, Agent, or Firm*—Millen, White, Zelano & Branigan, P.C.

(57) ABSTRACT

The invention relates to novel anthranilamide pyridinureas as VEGF receptor kinase inhibitors, their production and use as pharmaceutical agents for preventing or treating diseases that are triggered by persistent angiogenesis.

40 Claims, No Drawings

FOREIGN PATENT DOCUMENTS

| WO | WO 01/85691 A1 | 11/2001 | |
|----|----|----|----|
| WO | WO 01/85715 A | 11/2001 | |
| WO | WO 02/055501 A2 | 7/2002 | |
| WO | WO 02/066470 A1 | 8/2002 | |
| WO | WO 02/090352 A2 | 11/2002 | |
| WO | WO 03/040102 | 5/2003 | |
| WO | WO 03/048158 A1 | 6/2003 | |
| WO | WO 2004/013102 | 2/2004 | |
| WO | WO 2005/054179 | * 6/2005 | ............... 544/100 |

OTHER PUBLICATIONS

Strandtmann et al., J. Med. Chem. vol. 10, No. 6, 1967, pp. 1063-1065.

Sofina et al.: "Experimental Evaluation of Anti-Tumor Drugs in the USA and USSR and Clinical Correltaions," NCI Monograph 55, NIH Publication No. 80-1933 (1980).

Wermuth et al.: "The Practice of Medicinal Chemistry" Practice of Medicninal Chemistry XX, XX, 1996 pp. 203-237, XP002190259.

Montginoul et al.: "Analgesic, Anticonvulsant and Anti-Inflammatory Activities of 1H, 3H-Quinazoline-2,4-Diones" Chemical Abstracts Service, Coloumbus, Ohio, US; Retrieved from STN Database Accession No. 110:165551H; XP002135868; Ann. Pharm. FR (1989) vol. 46, No. 4, pp. 223-232.

Noda et al.: "Quinazoline Compounds" Chemical Abstracts, Jul. 19, 1976, vol. 85, No. 3, XP002135867.

Hardtmann et al.: "Chemistry of 2H-3, 1-Benzoxazine-2,4 (1H)-Dione (Isatoic Anhydrides). I. Synthesis of N-Substituted2H-3,1-Benzoxazine-2,4(1H)-Dione" Journal of Heterocyclic Chemistry, 1975, vol. 12, No. 3, pp. 565-572, Heterocorporation, XP002135866.

Pastor et al.: "Synthesis of new 1H,3H-Quinazoline-2,4-Diones", Bulletin de la Societe Chimique de France, vol 5-6, No. 2, 1975, pp. 1331-1338, XP002135865.

Manley et al.: "Anthranilic Acid Amides: a Novel Class of Antiangiogenic Vegf Receptor Kinase Inhibitors", J. Med. Chem., 2002, vol. 45, pp. 5687-5693.

Verweij et al.: "Multi-Tatget Tyrosine Kinase Inhibitiion: and the Winner is . . .", Journal of Clinical Oncology, vol. 25, No. 17, Jun. 10, 2007.

Hanrahan et al.: "Vascular Endothelial Growth Factor Receptor Tyrosine Kinase Inhibitors Vandetanib (ZD6474) and AZD217 in Lung Cancer", Cliical Cancer Search 2007; vol. 13 (15 Suppl) Aug. 1, 2007.

U.S. Appl. No. 10/631,018.

U.S. Appl. No. 11/525,091.

English Abstracts of Hardtmann et al.: "Chemistry of 2H-3,1-Benzoxazine-2,4 (1H)-Dione (Isatoic Anhydrides). I. Sythesis of N-Substituted2H-3,1-Benzoxazine-2,4(1H)-Dione" Journal of Heterocyclic Chemistry, 1975,vol. 12, No. 3, pp. 565-572, Heterocorporation, XP002135866.

English Abstracts of Pastor et al.: "Synthesis of New 1H,3H-Quinazoline-2,4-Diones", Bulletin de la Societe Chimique de France, vol. 5-6, No. 2, 1975, pp. 1331-1338, XP002135865.

Non Final Rejection Dated Dec. 5, 2008—U.S. Appl. No. 11/262,953, filed Nov. 2, 2005 (Publication No. 2006/0160861 A1).

Final Rejection Dated Dec. 17, 2008—U.S. Appl. No. 11/525,091, filed Sep. 22, 2006 (Publication No. 2007/0015794 A1).

Non Final Rejection Dated Mar. 17, 2008—U.S. Appl. No. 11/525,091, filed Sep. 22, 2006 (Publication No. 2007/0015794 A1).

Non Final Rejection Dated Oct. 8, 2008—U.S. Appl. No. 11/265,516, filed Nov. 3, 2005 (Publication No. 2006/0264426 A1).

Non Final Rejection Dated Dec. 6, 2005—U.S. Appl. No. 10/631,018, filed Jul. 31, 2003 (Publication No. 2004/0147535 A1).

Non Final Rejection Dated Nov. 24, 2004—U.S. Appl. No. 10/275,479, filed Jun. 23, 2003 (Publication No. 2004/00298880 A1).

Final Rejection Dated May 3, 2005—U.S. Appl. No. 10/275,480, filed Jun. 24, 2003 (Publication No. 2004/0102441 A1).

Non Final Rejection Dated Nov. 19, 2004—U.S. Appl. No. 10/275,480, filed Jun. 24, 2003 (Publication No. 2004/0102441 A1).

Non Final Rejection Dated Mar. 3, 2004—U.S. Appl. No. 10/275,480, filed Jun. 24, 2003 (Publicaiton No. 2004/0102441 A1).

Non Final Rejection Dated Apr. 2, 2007—U.S. Appl. No. 10/476,761, filed Aug. 25, 2004 (Publication No. 2004/0266770 A1).

Non Final Rejection Dated Feb. 21, 2002—U.S. Appl. No. 09/831,506, filed Sep. 14, 2001.

Non Final Rejection Dated Jun. 12, 2002—U.S. Appl. No. 09/831,506, filed Sep. 14, 2001.

Fnal Rejection Dated Dec. 30, 2002—U.S. Appl. No. 09/831,506, filed Sep. 14, 2001.

Non Final Rejection Dated Mar. 25, 2004—U.S. Appl. No. 09/831,506, filed Sep. 14, 2001.

Final Rejection Dated Dec. 9, 2008—U.S. Appl. No. 10/477,119, filed Jun. 23, 2004 (Publication No. 2004/0254185 A1).

Non Final Rejection Dated Mar. 11, 2008—U.S. Appl. No. 10/477,119, filed Jun. 23, 2004 (Publication No. 2004/0254185 A1).

Non Final Rejction Dated Nov. 14, 2008—U.S. Appl. No. 11/265,517, filed Nov. 3, 2005 (Publication No. 2006/0116380 A1).

Carmeliet et al.: "Angiogenesis in Cancer and Other Diseases"; MacMilliam Magazines Ltd., 2000, vol. 407, pp. 249-257.

English Abstract of JP 50157383 A.

English Abstract of DE 2652144 A.

English Abstract of EP 0564356 A1: 4-Phenylaminomethylimidazole Derivatives, Process for Their Preparation, Angiotensin II Receptor Antagonist and Their Application in Therapy [German] [French], Dodey, Pierre et al. Jan. 4, 1992.

* cited by examiner

ANTHRANILAMIDE PYRIDINUREAS AS VASCULAR ENDOTHELIAL GROWTH FACTOR (VEGF) RECEPTOR KINASE INHIBITORS

This application claims the benefit of the filing date of U.S. Provisional Application Ser. No. 60/626,919 filed Nov. 12, 2004 which is incorporated by reference herein.

The invention relates to novel anthranilamide pyridinureas as VEGF receptor kinase inhibitors, their production and use as pharmaceutical agents for preventing or treating diseases that are triggered by persistent angiogenesis.

Many diseases are known to be associated with persistent angiogenesis, for example, diseases such as tumor- or metastases-growth; psoriasis; arthritis, such as rheumatoid arthritis, hemangioma, endometriosis, angiofibroma; eye diseases, such as diabetic retinopathy, neovascular, glaucoma; renal diseases, such as glomerulonephritis, diabetic, nephropathy, malignant nephroscterosis, thrombotic microangiopathic syndrome, transplant rejections and glomerulopathy; fibrotic diseases, such as cirrhosis of the liver, mesangial cell proliferative diseases and arteriosclerosis.

Lymphangiogenesis is a process accompanying tumor growth and metastases. It is prominent in lymphedema, lymphangiectasia, lymphangioma, and lymphangiosarcoma and in asthmatic disease, where lymph vessels are chronically overexpressed in the lung.

Persistent angiogenesis is induced by the factor VEGF via its receptors. In order for VEGF to exert this action, it is necessary that VEGF bind to the receptor, and that a tyrosine phosphorylation is induced.

Direct or indirect inhibition of the VEGF receptor can be used for preventing or treating such diseases and other VEGF-induced pathological angiogenesis and vascular permeable conditions, such as tumor vascularization. For example, it is known that the growth of tumors can be inhibited by soluble receptors and antibodies against VEGF, an example for the tatter being Avastin® whose treatment paradigm has been introduced in human cancer therapy.

Anthranilic acid amides effective in the treatment of psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents; have been reported in WO 00/27820.

Anthranilic acid amides that are effective in the treatment of tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerutopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, as a support in scar-free healing, in senile keratosis and in contact dermatitis have also been reported in WO 04/13102.

There is, however, a desire to produce compounds that are as efficacious as possible in as broad a range of indications as possible. A constant blockade of VEGF mediated signal transduction is desirable in order to reduce persistent angiogenesis and lymphangiogenesis. Suitable compounds for longer term treatment should exhibit little or no drug-drug interaction potential. The Cytochrome P450 isoenzymes play a pivotal role in the degradation of pharmaceutical agents. The problem is also complicated by the fact that patients may express different relative amounts of the isoenzymes. An inhibition of these isoenzymes may result in undesirable pharmaceutical agent interactions, especially in the case of multimorbid patients (patients with multiple disease conditions). For example, inhibition of the Cytochrome P450 isoenzymes responsible for metabolisation of the parent agent could lead to toxic systemic concentrations. A further problem exists in combination therapy with other medications, whereby inhibition of the Cytochrome P450 isoenzymes responsible for metabolising the co-medications could lead to toxic systemic concentrations of the co-medication. This is especially the case for co-administered cytostatics in the case of cancer therapy.

Thus, it has now surprisingly been found that compounds of general formula (I), as described below, have more advantageous physico-chemical and/or pharmacokinetic properties and prevent, for example, tyrosine phosphorylation or stop persistent angiogenesis and thus the growth and propagation of tumors, whereby they are distinguished in particular by a potent inhibition of VEGF receptor kinases and a reduced potential for drug-drug interactions, specifically a reduced inhibition of cytochrome P450 isoenzymes 2C9 and 2C19.

The compounds of formula (I) are thus suitable, for example, for the treatment or prevention of diseases for which an inhibition of angiogenesis and/or the VEGF receptor kinases is beneficial.

In one aspect of the invention, there is provided an anthranilamide pyridinurea compound of formula (I):

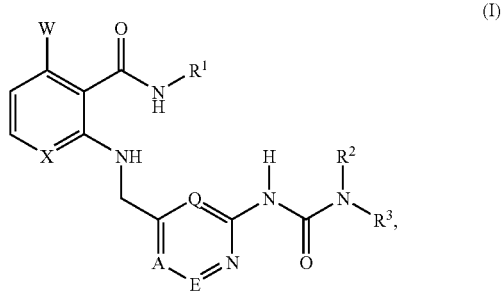

wherein

X is CH or N, preferably CH;

W is hydrogen or fluorine; preferably hydrogen;

A, E and Q independently of one another, are CH or N, whereby only a maximum of two nitrogen atoms are contained in the ring; preferably A, E, and Q are each CH;

$R^1$ is aryl or heteroaryl, which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$; preferably heteroaryl optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$; more preferably heteroaryl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$; even more preferably quinolinyl, isoquinolinyl, or indazolyl which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$; even further preferred quinolinyl, isoquinolinyl, or indazolyl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$; even further particularly preferred indazolyl substituted with $C_1$-$C_{12}$-alkyl, particularly 2-methyl-indazolyl and 1-methyl indazolyl;

$R^2$ and $R^3$ together with the nitrogen atom to which they are attached form a 3-8 membered heterocycloalkyl ring, preferably a 4-7 membered heterocycloalkyl ring, which may optionally contain at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, whereby $C_1$-$C_{12}$ alkyl optionally can also be substituted with a group —$OR^5$; more preferably, $R^2$ and $R^3$ together with the nitrogen atom to which they are attached form a 5 or 6 membered heterocycloalkyl ring, which contains no or at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$; whereby $C_1$-$C_{12}$ alkyl optionally can also be substituted with a group —$OR^5$;

$R^4$ is $C_1$-$C_{12}$-alkyl, $C_3$-$C_8$-cycloalkyl, aryl or heteroaryl; preferably $C_1$-$C_{12}$-alkyl; more preferably —$CH_3$;

$R^5$ is hydrogen, $C_1$-$C_{12}$-alkyl, $C_3$-$C_8$-cycloalkyl or halo-$C_1$-$C_6$-alkyl; preferably —$CH_3$ or hydrogen; more preferably hydrogen;

$R^6$ is hydrogen, $C_1$-$C_{12}$-alkyl, $C_3$-$C_8$-cycloalkyl, halo-$C_1$-$C_6$-alkyl, aryl, or —$NR^7R^8$; preferably $C_1$-$C_{12}$-alkyl or —$NR^7R^8$; more preferably —$CH_3$;

$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —$OR^5$ or —$N(CH_3)_2$, or $R^7$ and $R^8$ may also be chosen in such a way as to provide a 3-8 membered cycloalkyl ring, preferably a 4-7 membered cycloalkyl ring, more preferably a 5-6 membered cycloalkyl ring, which may optionally contain at least one further heteroatom, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O; —$OR^5$, $COR^6$, —$SR^4$, —$SOR^4$ or —$SO_2R^6$; preferably $R^7$ and $R^8$ independently of one another, are hydrogen, $COR^6$, —$SO_2R^6$, $C_1$-$C_{12}$-alkyl; more preferably hydrogen or $C_1$-$C_{12}$-alkyl; more preferably hydrogen or —$CH_3$, and as well as isomers, diastereoisomers, enantiomers, tautomers and salts thereof.

In a second aspect of the present invention, there is provided a pharmaceutical agent comprising at least one compound of formula (I) or an isomer, diastereoisomer, enantiomer, tautomer or salt thereof.

In a third aspect of the present invention, there is provided a pharmaceutical agent comprising at least one compound of formula (I) or an isomer, diastereoisomer, enantiomer, tautomer or salt thereof and at least one pharmaceutically acceptable carrier, dituent or excipient.

In a fourth aspect of the present invention there is provided a pharmaceutical agent comprising at least one compound of formula (I) or an isomer, diastereoisomer, enantiomer, tautomer or salt thereof for use in the prevention or treatment of diseases associated with persistent angiogenesis and/or diseases associated with excessive lymphangiogenesis.

In a fifth aspect of the present invention, there is provided a pharmaceutical agent comprising at least one compound of formula (I) or an isomer, diastereoisomer, enantiomer, tautomer or salt thereof for use in the prevention or treatment of tumor- or metastases-growth; psoriasis; Karposi's sarcoma; restenosis including stent-induced restenosis; Crohn's disease; Hodgkin's disease; leukemia; arthritis including rheumatoid arthritis, hemangioma, angiofibroma; endometriosis; eye diseases including diabetic retinopathy, neovascular glaucoma; corneal transplants; renal diseases, including glomerulonephritis, diabetic nephropathy, malignant nephrosclerosis, thrombotic microangiopathic syndrome, transplant rejections and glomerulopathy; fibrotic diseases, including cirrhosis of the liver; mesangial cell proliferative diseases; arteriosclerosis; injuries to the nerve tissue, and for inhibiting the reocclusion of vessels after balloon catheter treatment; in vascular prosthetics or after mechanical devices are used to keep vessels open, as immunosuppresive agent for supporting scar-free heating; senile keratosis; contact dermatitis; and asthma.

In a sixth aspect of the present invention, there is provided a pharmaceutical agent comprising at least one compound of formula (I) or an isomer, diastereoisomer, enantiomer, tautomer or salt thereof for use as VEGF receptor kinase 3-inhibitors of lymphangiogenesis.

In a seventh aspect of the present invention, there is provided a pharmaceutical agent comprising at least one compound of formula (I) or an isomer, diastereoisomer, enantiomer, tautomer or salt thereof for use in a method for the treatment of the human or animal body.

In an eighth aspect of the present invention, there is provided a pharmaceutical agent comprising at least one compound of formula (I) or an isomer, diastereoisomer, enantiomer, tautomer or salt thereof for use in the preparation of a pharmaceutical product for the prevention or treatment of a disease for which an inhibition of angiogenesis and/or lymphangiogenesis and/or the VEGF receptor kinases is beneficial.

In a ninth aspect of the present invention, there is provided a pharmaceutical agent comprising at least one compound of formula (I) or an isomer, diastereoisomer, enantiomer, tautomer or salt thereof for use as an inhibitor of the tyrosine kinases VEGFR-1 and VEGFR-2.

In a tenth aspect of the present invention, there is provided a compound of general formula (III):

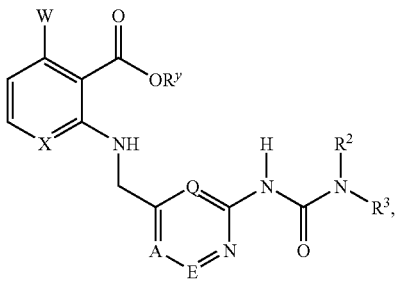

in which A, E, Q, W, X, R² and R³, are as defined for formula (I) supra and R$^y$ is H or $C_1$-$C_6$-alkyl, as an intermediate for the preparation of a compound of formula (I). Preferably, R$^y$ is H or $C_1$-$C_2$-alkyl, W is hydrogen and X is CH; more preferably, R$^y$ is H or —CH₃, W is hydrogen and X is CH.

In an eleventh aspect of the present invention, there is provided the use of a compound of general formula (III), in which A, E, Q, W, X, R² and R³ are as defined for formula (I) supra and R$^y$ is H or $C_1$-$C_6$-alkyl, as an intermediate for the preparation of a compound of formula (I).

In a twelfth aspect of the present invention, there is provided a process for the preparation of a compound of formula (I), wherein all substituents are as described in claim 1, in which a compound of formula (III), wherein A, E, Q, W, X, R² and R³ are as defined in claim 1 and R$^y$ is H or $C_1$-$C_6$-alkyl, is reacted with an amine of formula R¹NH₂ in which R¹ is as defined in claim 1.

In a thirteenth aspect of the present invention, there is provided a process for the preparation of a compound of formula (I), wherein all substituents are as described in claim 1, in which a compound of formula (II)

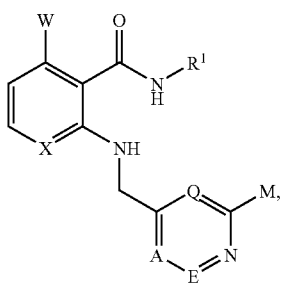

wherein A, E, Q, W, X, and R¹ are as defined in claim 1 and M stands for halogen, is:
(i) first converted to an amine and subsequently converted to a compound of formula (I) by reaction with a carbamoyl chloride of formula ClCONR²R³, wherein R² and R³ are as defined in claim 1; or, alternatively,
(ii) reacted with a compound of formula H₂NCONR²R³, wherein R² and R³ are as defined in claim 1, or alternatively,
(iii) first converted to an amine and subsequently converted to a compound of formula (I) by first reacting with a compound of formula ClCO₂Ph and then reacting with a compound of formula HNR²R³, wherein R² and R³ are as defined in claim 1. Preferably a compound of formula (I) is prepared using the (ii) process.

As used herein, the term "alkyl" is defined in each case as a substituted or unsubstituted straight-chain or branched alkyl group, such as, for example, methyl, ethyl, propyl, isopropyl, butyl, isobutyl, tert-butyl, pentyl, isopentyl or hexyl, heptyl, octyl, nonyl, decyl, undecyl, or dodecyl.

As used herein, the term "alkoxy" is defined in each case as a straight-chain or branched alkoxy group, such as, for example, methyloxy, ethyloxy, propyloxy, isopropyloxy, butyloxy, isobutyloxy, tert-butyloxy, pentyloxy, isopentyloxy, hexyloxy, heptyloxy, octyloxy, nonyloxy, decyloxy, undecyloxy or dodecyloxy.

As used herein, the term "cycloalkyl" is defined as a monocyclic alkyl ring, such as cyclopropyl, cyclobutyl, cyclopentyl, cyclohexyl, or cycloheptyl, cyclooctyl, cyclononyl or cyclodecyl, and also as bicyclic rings or tricyclic rings, such as, for example, adamantanyl. The cycloalkyl group may also contain, one or more heteroatoms, such as oxygen, sulphur and/or nitrogen, such that a heterocycloalkyl ring is formed.

As used herein, the term "heterocycloalkyl", as used throughout this text, e.g. as used in the definition of "R² and R³ together with the nitrogen atom to which they are attached form a 3-8 membered heterocycloalkyl ring" is defined as a nitrogen atom-containing monocyclic alkyl ring which optionally contains at least one further heteroatom, such as oxygen, sulphur and/or nitrogen, it being understood that said nitrogen atom Links the heterocycloalkyl ring to the rest of the molecule. Preferred are 3-8 membered heterocycloalkyl rings, preferably 4-7 membered heterocycloalkyl rings. Even more preferred are 5 or 6 membered heterocycloalkyl rings. For example, a heterocycloalkyl ring such as one selected from the following list can be mentioned

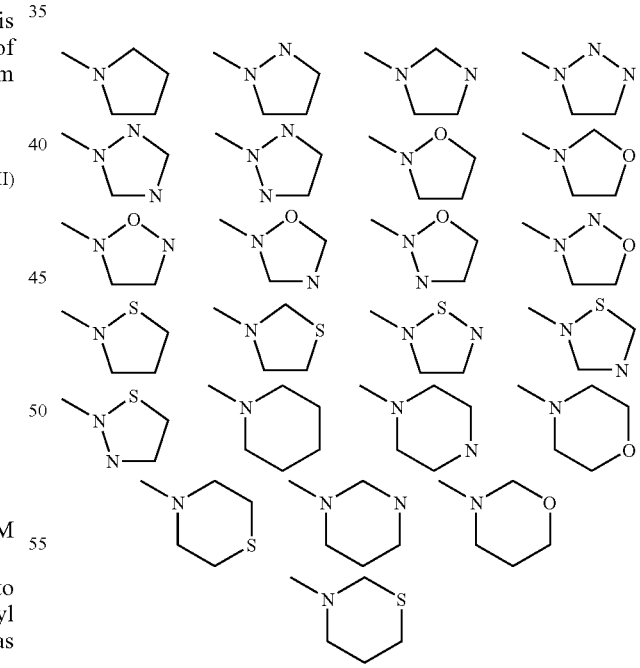

It is understood that any of the above structures may contain at least one additional heteroatom, such as nitrogen, oxygen or sulphur.

In particular, the following heterocycloalkyl rings can be mentioned: tetrahydrofuran, tetrahydropyran, pyrrolidine, piperidine, morpholine, piperazine and thiomorpholine. The heterocycloalkyl ring may be optionally substituted in one or more places in the same way or differently with, for example, halogen, cyano, $C_1$-$C_{12}$-alkyl, $C_1$-$C_{12}$-alkoxy, halo-$C_1$-$C_6$-alkyl, =O, —$OR^5$, —$SR^4$, —$SOR^4$ or —$SO_2R^6$, —$COR^6$, —$CO_2R^6$, whereby $C_1$-$C_{12}$ alkyl can optionally also be substituted with a group —$OR^5$. It is understood that the substitution on any of the above-mentioned heterocycloalkyl rings may take place on any one of the heterocycloalkyl ring's carbon atoms and/or on any one of the heterocycloalkyl ring's heteroatoms. Preferably the heterocycloalkyl ring is substituted in one or two places.

As used herein, the term "cycloalkenyl" is defined in each case as cyclobutenyl, cyclopentenyl, cyclohexenyl, cycloheptenyl, cyclooctenyl, cyclononenyl or cyclodecenyl, whereby the linkage can be carried out both to the double bond and to the single bonds.

As used herein, the term "halogen" is defined in each case as fluorine, chlorine, bromine or iodine, with fluorine being preferred for compounds of formula (I) and chlorine and bromine being preferred as substituent M in compounds of formula (II).

As used herein, the term "halo-$C_1$-$C_6$-alkyl" is defined as a $C_1$-$C_6$ alkyl group wherein some or all hydrogen atoms are replaced by halogen atoms, preferably replaced by one or more fluoro atoms. Preferred is the group $CF_3$.

As used herein, the term "alkenyl" is defined in each case as a straight-chain or branched alkenyl group that contains 2-6, preferably 2-4 carbon atoms. For example, the following groups can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-2-yl, but-1-en-3-yl, but-3-en-1-yl, and allyl.

As used herein, the term "aryl" is defined in each case as having 3 to 12 carbon atoms, preferably 6-12 carbon atoms, such as, for example, cyclopropenyl, cyclopentadienyl, phenyl, tropyl, cyclooctadienyl, indenyl, naphthyl, azutenyl, biphenyl, fluorenyl, anthracenyl etc, phenyl being preferred.

As used herein, the term "$C_1$-$C_{12}$", as used throughout this text e.g. in the context of the definitions of "$C_1$-$C_{12}$-alkyl" and "$C_1$-$C_{12}$-alkoxy", is to be understood as meaning an alkyl or alkoxy group having a finite number of carbon atoms of 1 to 12, i.e. 1, 2, 3, 4, 5, 6, 7, 8, 9, 10, 11 or 12 carbon atoms. It is to be understood further that said term "$C_1$-$C_{12}$" is to be interpreted as any subrange comprised therein, e.g. $C_1$-$C_{12}$, $C_2$-$C_{11}$, $C_3$-$C_{10}$, $C_4$-$C_9$, $C_5$-$C_8$, $C_6$-$C_7$, $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, $C_1$-$C_{11}$; preferably $C_1$-$C_2$, $C_1$-$C_3$, $C_1$-$C_4$, $C_1$-$C_5$, $C_1$-$C_6$; more preferably $C_1$-$C_3$.

Similarly, as used herein, the term "$C_2$-$C_6$", as used throughout this text e.g. in the context of the definitions of "$C_2$-$C_6$-alkenyl", is to be understood as meaning an alkenyl group having a finite number of carbon atoms of 2 to 6, i.e. 2, 3, 4, 5, or 6 carbon atoms. It is to be understood further that said term "$C_2$-$C_6$" is to be interpreted as any subrange comprised therein, e.g. $C_2$-$C_6$, $C_3$-$C_5$, $C_3$-$C_4$, $C_2$-$C_3$, $C_2$-$C_4$, $C_2$-$C_5$; preferably $C_2$-$C_3$.

Further as used herein, the term "$C_1$-$C_6$", as used throughout this text e.g. in the context of the definitions of "halo-$C_1$-$C_6$-alkyl", is to be understood as meaning a haloalkyl group having a finite number of carbon atoms of 1 to 6, i.e. 1, 2, 3, 4, 5, or 6 carbon atoms. It is to be understood further that said term "$C_1$-$C_6$" is to be interpreted as any subrange comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$ more preferably $C_1$-$C_3$.

As used herein, the term "heteroaryl" as defined in each case, is an aromatic ring system which contains, in the ring, at least one heteroatom which may be identical or different, and which comprises 3-16 ring atoms, preferably 5 or 6 atoms or 9 or 10 atoms, said heteroatom being such as oxygen, nitrogen or sulphur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, e.g., quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc. More preferably, the heteroaryl is selected from quinolinyl, isoquinolinyl, or indazolyl. More preferably still, the heteroaryl is indazolyl.

As used herein, the term "$C_1$-$C_3$-dialkyl ketal" is formed when two $C_1$-$C_3$-alkoxy groups are bonded, preferably via their oxygen atoms, to the same carbon atom. Preferably, the $C_1$-$C_3$-alkoxy group is —$OCH_3$.

As used herein, the term "$C_1$-$C_3$-cyclic ketal" is defined as a 5-6 membered ring formed when a $C_1$-$C_3$-dioxyalkyl group such as ethan-1,2-dioxy or propan-1,3-dioxy is bonded via the oxygen atoms to the same carbon atom. Examples of $C_1$-$C_3$-cyclic ketals are 1,3-dioxolane or 1,3-dioxane rings. Preferably, $C_1$-$C_3$-cyclic ketal is —$O(CH_2)_2O$— such that a 1,3-dioxolane ring is formed.

The aryl group and the heteroaryl group in each case can be substituted in the same way or differently in one or more places with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$. It is understood that the substitution on the aryl group and the heteroaryl group may take place on any one of the group's carbon atoms and/or on any one of the heteroatoms. Preferably the aryl group and the heteroaryl group is substituted in one or two places.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol.

If a basic group is included, the physiologically compatible salts of organic and inorganic acids are suitable, such as hydrochloric acid, sulphuric acid, phosphoric acid, citric acid, tartaric acid, succinic acid, fumaric acid.

The compounds of general formula (I) according to the invention also contain the possible tautomeric forms and comprise the E-isomers or Z-isomers, or, if one or more stereogenic centers are present, racemates and/or enantiomers and/or diastereoisomers. Thus, a molecule with a single stereogenic center may be a mixture of enantiomers (R,S), or may be a single (R) or (S) enantiomer. A molecule with more than one stereogenic center may be a mixture of diastereoisomers, or may be a single diastereoisomer, whereby the diastereoisomers may also exist as mixtures of enantiomers or single enantiomers.

One embodiment of the present invention are compounds of formula (I) wherein X is CH.

In one embodiment, W is hydrogen.

In one embodiment, A, E, and Q are each CH.

In one embodiment, X is CH, W is hydrogen, and A, E, and Q each are CH.

In one embodiment, $R^1$ is aryl or heteroaryl, which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$.

In another embodiment, $R^1$ is heteroaryl optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$. In a preferred embodiment, $R^1$ is heteroaryl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$. In a more preferred embodiment, $R^1$ is quinolinyl, isoquinolinyl, or indazolyl which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$. In an even more preferred embodiment, $R^1$ is quinolinyl, isoquinolinyl, or indazolyl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$. In an even more particularly preferred embodiment, $R^1$ is indazolyl substituted with $C_1$-$C_{12}$-alkyl, particularly $R^1$ is 2-methyl-indazolyl or 1-methyl indazolyl.

In one embodiment, $R^2$ and $R^3$ together with the nitrogen atom to which they are attached form a 5 or 6 membered heterocycloalkyl ring, which contains no or at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, whereby $C_1$-$C_{12}$ alkyl optionally can also be substituted with a group —$OR^5$.

In one embodiment, $R^4$ is $C_1$-$C_{12}$-alkyl. In a preferred embodiment, $R^4$ is —$CH_3$.

In one embodiment, $R^5$ is —$CH_3$ or hydrogen. In a preferred embodiment, $R^5$ is hydrogen.

In one embodiment, $R^6$ is $C_1$-$C_{12}$-alkyl or —$NR^7R^8$. In a preferred embodiment, $R^6$ is $C_1$-$C_{12}$-alkyl. In a more preferred embodiment, $R^6$ is —$CH_3$.

In one embodiment, $R^7$ and $R^8$ independently of one another, are hydrogen, $COR^6$, $SO_2R^6$, $C_1$-$C_{12}$-alkyl. In a preferred embodiment, $R^7$ and $R^8$ independently of one another are hydrogen or —$CH_3$.

In one embodiment
X is CH,
W is hydrogen,
A, E and Q each are CH,
$R^1$ is aryl or, heteroaryl, which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$,
$R^2$ and $R^3$ together with the nitrogen atom to which they are attached form a 3-8 membered heterocycloalkyl ring, preferably a 4-7 membered heterocycloalkyl ring, more preferably a 5 or 6 membered heterocycloalkyl ring, which may optionally contain at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, whereby $C_1$-$C_{12}$ alkyl optionally can also be substituted with a group —$OR^5$,
$R^4$ is $C_1$-$C_{12}$-alkyl, $C_3$-$C_8$-cycloalkyl, aryl or heteroaryl,
$R^5$ is hydrogen, $C_1$-$C_{12}$-alkyl, $C_3$-$C_8$-cycloalkyl or halo-$C_1$-$C_6$-alkyl,
$R^6$ hydrogen, $C_1$-$C_{12}$-alkyl, $C_3$-$C_8$-cycloalkyl, halo-$C_1$-$C_6$-alkyl, aryl, or —$NR^7R^8$,
$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —$OR^5$ or —$N(CH_3)_2$, or $R^7$ and $R^8$ may also be chosen in such a way as to provide a 3-8 membered cycloalkyl ring, preferably a 4-7 membered cycloalkyl ring, more preferably a 5-6 membered cycloalkyl ring, which may optionally contain at least one further heteroatom, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo $C_1$-$C_6$-alkyl, =O, —$OR^5$, $COR^6$, —$SR^4$, —$SOR^4$ or —$SO_2R^6$, and as well as isomers, diastereoisomers, enantiomers, tautomers and salts thereof.

In a preferred embodiment
X is CH,
W is hydrogen,
A, E and Q each are CH,
$R^1$ is heteroaryl, which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, whereby $C_1$-$C_{12}$-alkyl may be substituted with —$NR^7R^8$,
$R^2$ and $R^3$ together with the nitrogen atom to which they are attached form a 3-8 membered heterocycloalkyl ring, preferably a 4-7 membered heterocycloalkyl ring, more preferably a 5 or 6 membered heterocycloalkyl ring, which may optionally contain at least one further heteroatom, such as nitrogen, oxygen or sulphur, and which may be optionally substituted in one or more places in the same way, or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, whereby $C_1$-$C_{12}$ alkyl optionally can also be substituted with a group —$OR^5$;
$R^4$ is $C_1$-$C_{12}$-alkyl, $C_3$-$C_8$-cycloalkyl, aryl or heteroaryl,
$R^5$ is hydrogen, $C_1$-$C_{12}$-alkyl, $C_3$-$C_8$-cycloalkyl or halo-$C_1$-$C_6$-alkyl,
$R^6$ hydrogen, $C_1$-$C_{12}$-alkyl, $C_3$-$C_8$-cycloalkyl, halo-$C_1$-$C_6$-alkyl, aryl, or —$NR^7R^8$;
$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —$OR^5$ or —$N(CH_3)_2$, or $R^7$ and $R^8$ may also be chosen in such a way as to provide a 3-8 membered cycloalkyl ring, preferably a 4-7 membered cycloalkyl ring, more preferably a 5-6 membered cycloalkyl ring, which may optionally contain at least one further heteroatom, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, COR$^6$, —SR$^4$, —SOR$^4$ or —SO$_2$R$^6$, and as well as isomers, diastereoisomers, enantiomers, tautomers and salts thereof.

In a further preferred embodiment

X is CH,

W is hydrogen,

A, E and Q each are CH,

R$^1$ is quinolinyl, isoquinolinyl, or indazolyl which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, whereby $C_1$-$C_{12}$-alkyl may be substituted with —NR$^7$R$^8$, R$^2$ and R$^3$ together with the nitrogen atom to which they are attached form a 3-8 membered heterocycloalkyl ring, preferably a 4-7 membered heterocycloalkyl ring, more preferably a 5 or 6 membered heterocycloalkyl ring, which may optionally contain at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR$^5$, —SR$^4$, —SOR$^4$, —SO$_2$R$^6$, —COR$^6$ or —CO$_2$R$^6$, whereby $C_1$-$C_{12}$ alkyl optionally can also be substituted with a group —OR$^5$;

R$^4$ is $C_1$-$C_{12}$-alkyl, $C_3$-$C_8$-cycloalkyl, aryl or heteroaryl,

R$^5$ is hydrogen, $C_1$-$C_{12}$-alkyl, $C_3$-$C_8$-cycloalkyl or halo-$C_1$-$C_6$-alkyl, R$^6$ hydrogen, $C_1$-$C_{12}$-alkyl, $C_3$-$C_8$-cycloalkyl, halo-$C_1$-$C_6$-alkyl, aryl, or —NR$^7$R$^8$, R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —OR$^5$ or —N(CH$_3$)$_2$, or R$^7$ and R$^8$ may also be chosen in such a way as to provide a 3-8 membered cycloalkyl ring, preferably a 4-7 membered cycloalkyl ring, more preferably a 5-6 membered cycloalkyl ring, which may optionally contain at least one further heteroatom, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, COR$^6$, —SR$^4$, —SOR$^4$ or —SO$_2$R$^6$, and as well as isomers, diastereoisomers, enantiomers, tautomers and salts thereof.

In a more preferred embodiment

X is CH,

W is hydrogen,

A, E and Q each are-CH,

R$^1$ is quinolinyl, isoquinolinyl, or indazolyl which is substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, whereby $C_1$-$C_{12}$-alkyl may be substituted with —NR$^7$R$^8$, R$^2$ and R$^3$ together with the nitrogen atom to which they are attached form a 5 or 6 membered heterocycloalkyl ring, which may optionally contain at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR$^5$, —SR$^4$, —SOR$^4$, —SO$_2$R$^6$, —COR$^6$ or —CO$_2$R$^6$, whereby $C_1$-$C_{12}$ alkyl optionally can also be substituted with a group —OR$^5$;

R$^4$ is $C_1$-$C_{12}$-alkyl, $C_3$-$C_8$-cycloalkyl, aryl or heteroaryl,

R$^5$ is hydrogen, $C_1$-$C_{12}$-alkyl, $C_3$-$C_8$-cycloalkyl or halo-$C_1$-$C_6$-alkyl, R$^6$ hydrogen, $C_1$-$C_{12}$-alkyl, $C_3$-$C_8$-cycloalkyl, halo-$C_1$-$C_6$-alkyl, aryl, or —NR$^7$R$^8$, R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —OR$^5$ or —N(CH$_3$)$_2$, or R$^7$ and R$^8$ may also be chosen in such a way as to provide a 3-8 membered cycloalkyl ring, preferably a 4-7 membered cycloalkyl ring, more preferably a 5-6 membered cycloalkyl ring, which may optionally contain at least one further heteroatom, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, COR$^6$, —SR$^4$, —SOR$^4$ or —SO$_2$R$^6$, and as well as isomers, diastereoisomers, enantiomers, tautomers and salts thereof.

In an even more preferred embodiment

X is CH,

W is hydrogen,

A, E and Q each are CH,

R$^1$ is indazolyl which may be optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, whereby $C_1$-$C_{12}$-alkyl may be substituted with —NR$^7$R$^8$, R$^2$ and R$^3$ together with the nitrogen atom to which they are attached form a 5 or 6 membered heterocycloalkyl ring, which may optionally contain at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR$^5$, —SR$^4$, —SOR$^4$, —SO$_2$R$^6$, —COR$^6$ or —CO$_2$R$^6$, whereby $C_1$-$C_{12}$ alkyl optionally can also be substituted with a group —OR$^5$;

R$^4$ is $C_1$-$C_{12}$-alkyl, $C_3$-$C_8$-cycloalkyl, aryl or heteroaryl,

R$^5$ is hydrogen, $C_1$-$C_{12}$-alkyl, $C_3$-$C_8$-cycloalkyl or halo-$C_1$-$C_6$-alkyl, R$^6$ hydrogen, $C_1$-$C_{12}$-alkyl, $C_3$-$C_8$-cycloalkyl, halo-$C_1$-$C_6$-alkyl, aryl, or —NR$^7$R$^8$, R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl, or $C_1$-$C_{12}$-alkoxy, whereby $C_1$-$C_{12}$-alkyl may be optionally substituted with —OR$^5$ or —N(CH$_3$)$_2$, or R$^7$ and R$^8$ may also be chosen in such a way as to provide a 3-8 membered cycloalkyl ring, preferably a 4-7 membered cycloalkyl ring, more preferably a 5-6 membered cycloalkyl ring, which may optionally contain at least one further heteroatom, such as nitrogen, oxygen or sulphur, and may be optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, COR$^6$, —SR$^4$, —SOR$^4$ or —SO$_2$R$^6$, and as well as isomers, diastereoisomers, enantiomers, tautomers and salts thereof.

In an even more-preferred embodiment:

X is CH,

W is hydrogen,

A, E and Q each are CH,

R¹ is indazolyl substituted with $C_1$-$C_{12}$-alkyl, optionally having a halogen atom substituent, R² and R³ together with the nitrogen atom to which they are attached form a 5 or 6 membered heterocycloalkyl ring, which may optionally contain at least one further heteroatom, such as nitrogen, oxygen or sulphur, and which may be optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR⁵, —SR⁴, —SOR⁴, —SO₂R⁶, —COR⁶ or —CO₂R⁶, whereby $C_1$-$C_{12}$ alkyl optionally can also be substituted with a group —OR⁵;

R⁴ is $C_1$-$C_{12}$-alkyl,

R⁵ is hydrogen,

R⁶ is $C_1$-$C_{12}$-alkyl, and as well as isomers, diastereoisomers, enantiomers, tautomers and salts thereof.

Some specific examples of compounds of the present invention include the following:

4-hydroxy-4-methyl-piperidine-1-carboxylic acid (4-{[2-(2-methyl-2H-indazol-6-ylcarbamoyl)-phenylamino]-methyl}-pyridin-2-yl)-amide, 4-hydroxy-piperidine-1-carboxylic acid (4-{[2-(2-methyl-2H-indazol-6-ylcarbamoyl)-phenylamino]-methyl}-pyridin-2-yl)-amide, 4-hydroxy-4-trifluoromethyl-piperidine-1-carboxylic acid (4-{[2-(2-methyl-2H-indazol-6-ylcarbamoyl)-phenylamino]-methyl}-pyridin-2-yl)-amide, 1-oxo-thiomorpholine-4-carboxylic acid (4-{[2-(2-methyl-2H-indazol-6-ylcarbamoyl)-phenylamino]-methyl}-pyridin-2-yl)-amide, 1,1-dioxo-thiomorpholine-4-carboxylic acid (4-{[2-(2-methyl-2H-indazol-6-ylcarbamoyl)-phenylamino]-methyl}-pyridin-2-yl)-amide, 4-methyl-piperazine-1-carboxylic acid (4-{[2-(2-methyl-2H-indazol-6-ylcarbamoyl)-phenylamino]-methyl}-pyridin-2-yl)-amide, 4-methyl-piperazine-1-carboxylic acid (4-{[2-(1-methyl-1H-indazol-6-ylcarbamoyl)-phenylamino]-methyl}-pyridin-2-yl)-amide, 4-(2-hydroxy-ethyl)-piperazine-1-carboxylic acid (4-{[2-(1-methyl-1H-indazol-6-ylcarbamoyl)-phenylamino]-methyl}-pyridin-2-yl)-amide, 4-(2-hydroxy-ethyl)-piperazine-1-carboxylic acid (4-{[2-(2-methyl-2H-indazol-6-ylcarbamoyl)-phenylamino]-methyl}-pyridin-2-yl)-amide, 4-methanesulfonyl-piperazine-1-carboxylic acid (4-{[2-(2-methyl-2H-indazol-6-ylcarbamoyl)-phenylamino]-methyl}-pyridin-2-yl)-amide, morphotine-4-carboxylic acid (4-{[2-(1-methyl-1 H-indazol-6-ylcarbamoyl)-phenylamino]-methyl}-pyridin-2-yl)-amide, morpholine-4-carboxylic acid (4-{[2-(2-methyl-2H-indazol-6-ylcarbamoyl)-phenylamino]-methyl}-pyridin-2-yl)-amide, morpholine-4-carboxylic acid (4-{[2-(7-methoxy-isoquinolin-3-ylcarbamoyl)-phenylamino]-methyl}-pyridin-2-yl)-amide, 2,6-dimethyl-morpholine-4-carboxylic acid (4-{[2-(1-methyl-1H-indazol-6-ylcarbamoyl)-phenylamino]-methyl}-pyridin-2-yl)-amide, 2,6-dimethyl-morpholine-4-carboxylic acid (4-{[2-(2-methyl-2H-indazol-6-ylcarbamoyl)-phenylamino]-methyl}-pyridin-2-yl)-amide, 3-hydroxy-pyrrolidine-1-carboxylic acid (4-{[2-(2-methyl-2H-indazol-6-ylcarbamoyl)-phenylamino]-methyl}-pyridin-2-yl)-amide, morpholine-4-carboxylic acid (4-{[3-fluoro-2-(2-methyl-2H-indazol-6-ylcarbamoyl)-phenylamino]-methyl}-pyridin-2-yl)-amide, morpholine-4-carboxylic acid (4-{[2-(isoquinolin-3-ylcarbamoyl)-phenylamino]-methyl}-pyridin-2-yl)-amide, morpholine-4-carboxylic acid (4-{[2-(3,6-difluoro-quinolin-2-ylcarbamoyl)-phenylamino]-methyl}-pyridin-2-yl)-amide, and morpholine-4-carboxylic acid (4-{[2-(3-fluoro-6-methoxy-quinolin-2-ylcarbamoyl)-phenylamino]-methyl}-pyridin-2-yl)-amide The compounds of formula (I) can be used as pharmaceutical agents based on their inhibitory activity relative to the phosphorylation of VEGF receptors. Based on their profile of action, the compounds according to the invention are suitable for preventing or treating diseases that are caused or promoted by persistent angiogenesis.

Since the compounds of formula (I) are identified as inhibitors of the tyrosine kinases VEGFR-1 and VEGFR-2, they are suitable in particular for preventing or treating those diseases that are caused or promoted by persistent angiogenesis that is triggered via the VEGF receptor or by an increase in vascular permeability.

The present invention also provides the use of the compounds of formula (I) as inhibitors of the tyrosine kinases VEGFR-1 and VEGFR-2, or KDR and FLT.

The term "diseases that are caused or promoted by persistent angiogenesis" relates especially to diseases such as tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; corneal transplants; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis, in contact dermatitis, and in asthma.

In treating injuries to nerve tissue, quick scar formation on the injury sites can be prevented with the compounds according to the invention, i.e., scar formation is prevented from occurring before the axons reconnect. A reconstruction of the nerve compounds can be thus facilitated.

The formation of ascites in patients, especially patients suffering from tumors caused by metastases, can also be suppressed with the compounds according to the invention VEGF-induced oedemas can also be suppressed.

By a treatment with the compounds of formula (I), not only a reduction of the size of metastases but also a reduction of the number of metastases can be achieved.

Lymphangiogenesis plays an important role in lymphogenic metastasis (Karpanen, T. et at., Cancer Res. Mar. 1, 2001, 61(5): 1786-90, Veikkola, T., et at., EMBO J. Mar. 15, 2001; 20 (6): 1223-31).

The compounds of formula (I) also show excellent action as VEGFR kinase 3 inhibitors and are, therefore, also suitable as effective inhibitors of lymphangiogenesis.

The compounds of formula (I) are thus effective in the prevention or treatment of diseases that are associated with excessive lymphangiogenesis, such as lymphedema, lymphangiectasia, lymphangioma, and lymphangiosarcoma but also asthma. Lymphatic growth around tumors may facilitate metastatic spread of malignant cells that ultimately kill the patient. This process can be effectively hindered by the compounds of this invention. Thus the compounds are not only effective in inhibiting metastasis growth, but can also be effective in reducing the number of metastases.

This invention also provides the use of the compounds of formula (I) as inhibitors of the tyrosine kinase VEGFR-3 (FLT-4).

A further object of this invention is also a pharmaceutical agent for preventing or treating diseases that are associated with excessive lymphangiogenesis, such as metastasis growth, lymphedema, lymphangiectasia, lymphangioma, and lymphangiosarcoma but also asthma.

Furthermore, the invention relates to the use of the compounds of general formula (I) for the preparation of a pharmaceutical agent for use in or for the prevention or treatment of tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; corneal transplants; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis, in contact dermatitis, and also in asthma.

To use the compounds of formula (I) as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, capsules or in liquid form, for example as solutions, suspensions or emulsions. They also can contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch are suitable. The administration can also be carried out in liquid form, such as, for example, as juice, to which optionally a sweetener or, if necessary, one or more flavoring substances, is added.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into 2 or more daily doses.

A further object of this invention is therefore a pharmaceutical agent comprising a compound of formula (I) in combination with at least one pharmaceutically acceptable carrier or excipient.

Compounds of formula (I) are obtained, in that a compound of general formula (II):

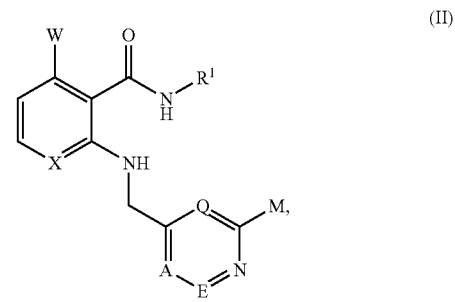

(II)

in which A, E, Q, W, X and $R^1$ are defined supra as for general formula (I) and M stands for halogen, is (i) first converted to an amine and then, by reaction with a carbamoyl chloride of formula $ClCONR^2R^3$ in which $R^2$ and $R^3$ are defined supra as for general formula (I), is converted to a urea of general formula (I), or (ii) reacted with a urea of general formula $H_2NCONR^2R^3$ in which $R^2$ and $R^3$ are defined supra as for general formula (I), or (iii) first converted to an amine, then converted to a compound of formula (I) by first reacting with a compound of formula $ClCO_2Ph$ and then reacting with a compound of formula $HNR^2R^3$, wherein $R^2$ and $R^3$ are defined supra as for general formula (I); or a compound of general formula (III) in which A, E, Q, W, X, $R^2$, and $R^3$ are defined as for general formula (I) and $R^y$ stands for H or $C_1$-$C_6$-alkyl, is reacted with an amine of general formula $R^1NH_2$ in which $R^1$ is defined supra as for general formula (I)

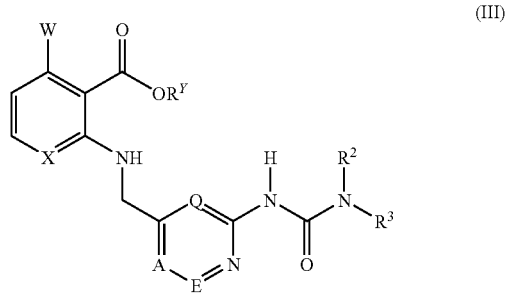

(III)

There are many methods known to the person skilled in the art in the literature for amide formation.

For example, it is possible to start from the corresponding ester. The ester may be reacted according to J. Org. Chem. 1995, 8414 with trimethylaluminium and the corresponding amine in solvents such as toluene or 1,2-dichloroethane, at temperatures of 0° C. to the boiling point of the solvent. If the molecule contains two ester groups, both are converted into the same amide. Instead of trimethylaluminium, sodium hexamethyldisilazide can also be used.

For amide formation, however, all processes that are known to the person skilled in the art from peptide chemistry are also available. For example, the corresponding acid, obtained from the corresponding ester by saponification, can be reacted with the amine in aprotic polar solvents, such as, for example, dimethylformamide, via an activated acid derivative, obtainable, for example, with hydroxybenzotriazole and a carbodiimide, such as, for example, diisopropylcarbodiimide, at temperatures of between 0° C. and the boiling point of the solvent, preferably at 80° C., or else with preformed reagents, such as, for example, HATU (O-(7-azabenzotriazol-1-yl)-1,1,3,3-tetramethyluronium hexafluorophosphate) (Chem. Comm. 1994, 201), at temperatures of between 0° C. and the boiling point of the solvent, preferably at room temperature. The addition of a base such as N-methylmorpholine, for example, is necessary. Amide formation, may also be accomplished via the acid halide, mixed acid anhydride, imidazolide or azide.

The ureas of aryl- or heteroaryl amines may be prepared by a variety of literature known methods, known to the person skilled in the art. For example, they may be prepared by the reaction of aryl- or heteroaryl amines with isocyanates, the reaction of amines with aryl- or heteroaryl-carbamates such as aryl- or heteroaryl-phenoxycarbamates, or the reaction of aryl- or heteroaryl amines with appropriately substituted carbamoyl chlorides, or the reaction of an aryl- or heteroaryl-halide with ureas under the influence of metal catalysis.

For example, the ureas of aminopyridines may be prepared by reacting a urea with halopyridines, whereby chloro and bromopyridines are preferred, under the catalytic influence of metal complexes, for example, palladium- or copper complexes. In the case of copper complexes the use of stoichiometric amounts of the copper complexes may be advantageous for the reaction outcome. Suitable copper salts for the reaction are copper (I) or copper (II) salts whereby copper (I) salts such as, for example, copper (I) oxide or copper (I) iodide, are preferred. In the case of copper (I) iodide the addition of an additive such as, for example, ethylenediamine is necessary. Suitable solvents for this copper-promoted coupling are dioxane or dimethylformamide, at temperatures upto the boiling point of the solvents, whereby 120° C. is preferred. Addition of a base is also necessary, such as potassium phosphate or cesium carbonate. In the case of palladium catalysis, palladium complexes is such as tris-(dibenzylideneacetone) -dipalladium(0) maybe employed. Suitable solvents for the reaction are toluene, dioxane or dimethylformamide, whereby mixtures of solvents may also be advantageous for the reaction, at temperatures from room temperature to the boiling points of the solvents, whereby 110° C. is preferred. A co-ligand such as BINAP, DPPF or xantphos is also employed. A base is also required, suitable bases for the reaction are for example, cesium carbonate, potassium phosphate or sodium tert-butoxide. The required urea starting materials for the above copper or palladium promoted coupling may in turn be prepared from the reaction of the corresponding amines with the corresponding isocyanates. Solvents such as, for example, dichloromethane, or, isopropylalcohol may be employed at temperatures from 0° C. to the boiling points of the solvents, whereby room temperature is preferred.

Methods for the preparation of substituted or unsubstituted 6-aminoindazoles are well known to the person skilled in the art in the literature. They may be obtained from the reduction of the corresponding nitroindazoles via catalytic hydrogenation or other reduction methods well known to the person skilled in the art. N-alkylation of substituted nitroindazoles may be accomplished with a variety of literature-known alkylating agents. For example, methylation of N-1 or N-2 of a suitably functionalised 6-nitroindazole may be accomplished by, for example, treatment with a base, preferably $Cs_2CO_3$ or NaH, and a methyl halide, preferably methyl iodide in a suitable solvent such as N,N-dimethylformamide, at temperatures ranging from 0° C. to 50° C., whereby 50° C. is preferred. 3-Substituted-6-nitroindazoles may be prepared by a variety of methods. For example alkyl substituents may be introduced in the 3-position by way of standard Suzuki reactions between an appropriate 3-haloindazole, whereby the appropriate 3-iodoindazoles are preferred, and an alkyl boronic acid, whereby the trialkylboraxines may also be employed. N-protection of the indazole may be advantageous for the reaction. 6-Nitroindazole-3-carboxylic acid provides a suitable starting material for ester, amide, hydroxymethyl and alkoxymethyl substitution in the 3-position of 6-nitroindazole, via well known transformations such as transesterification, amide coupling, reduction, or reduction followed by alkylation. 6-Nitroindazole-3-carbaldehyde (prepared by the reaction of commercial 6-nitroindole with $NaNO_2$ in the presence of dilute aqueous hydrochloric acid according to J. Med. Chem. 2001, 44, 7, 1021) provides a useful precursor to 6-nitroindazole-3-carboxylic acid via oxidation methods well known to the person skilled in the art. In turn, 6-nitroindazole-3-carbaldehyde may also be converted to 3-hydroxymethyl-6-nitroindazole, 3-alkoxymethyl-6-nitroindazole, or 3-aminomethyl-6-nitroindazole derivatives by equally standard transformations such as reduction, reduction followed by alkylation, or reductive amination. Such standard transformations may also be applied to the synthesis of other substituted aminoindazoles. A variety of substituted nitroindazoles are commercially available, however they may be readily synthesised via the reaction of a suitable 2-aminonitrotoluene derivative with, for example, $NaNO_2$ and aqueous hydrochloric acid. If required, the nitro group may be introduced after the cyclisation reaction of a suitable 2-aminotoluene derivative by standard nitration chemistry.

The preparation of N-alkylated-aminobenzimidazoles may be accomplished from the corresponding N-alkylated-nitrobenzimidazoles via standard reduction chemistry. Alkylation of a suitable functionalised nitrobenzimidazole, for example with an alkyl halide and a base, furnishes N1- and N3-alkylated-nitrobenzimidazoles, which may be separated and isolated in pure form by standard purification techniques. For example, 6-amino-1-methyl-benzimidazole may be produced by the reaction of commercial 5-nitrobenzimidazole with MeI and $Cs_2CO_3$ in DMF followed by purification (of the resulting mixture of 5- and 6-nitro-1-methyl-benzimidazoles) and hydrogenation in the presence of 10% Pd on charcoal. Similarly, the preparation of N-alkylated-aminobenzotriazoles may also be accomplished from the corresponding nitrobenzotriazoles. Alkylation of a suitable functionalised nitrobenzotriazole, for example with an alkyl halide and a base, furnishes N1-, N2- and N3-alkylated-nitrobenzotriazoles, which may be separated and isolated in pure form by standard purification techniques. Standard reduction chemistry furnishes the corresponding aminobenzotriazoles. For example, 5-amino-2-methyl-benzotriazole may be prepared according to a literature procedure (Eur. J. Med. Chem. 1992, 27, 161-166).

The preparation of 3-aminoisoquinolines which are substituted in the 7-position, may be accomplished via the corresponding 3-amino-1-bromo-7-substituted isoquinoline by way of reductive dehalogenation. 3-amino-1-bromo-7-substituted isoquinolines may in turn be prepared by the reaction of a suitable 2-cyano-4-substituted-benzeneacetonitrile with HBr in acetic acid. For example, 3-amino-7-methoxyisoquinoline may be prepared in two steps (HBr mediated cyclisation followed by reductive dehalogenation) from 2-cyano-4-methoxy-benzeneacetonitrile, which may be prepared according to a literature procedure (Bull. Chem. Soc. Jpn. 1980, 53, 10, 2885-2890).

1-Alkyl-6-amino-quinolin-2-ones may be prepared by known methods. For example, 6-amino-2-methyl-quinolin-2-one may be prepared according to a literature procedure (J. Chem. Research, Synopses, 1997, 310-311). 2-Amino-3,6-disubstituted quinolines may be prepared by a number of procedures. For example, the reaction of the lithium salt (generated with a base such as lithium diisopropylamide) of a suitably substituted cyanomethyl-dialkylphosphonate with a suitably substituted 2-nitrobenzaldehyde derivative in a suitable solvent, such as THF, furnishes a suitable acrylonitrile derivative which may be cyclised to the desired 2-amino-3,6-disubstituted quinoline by treating with a suitable reducing agent, such as iron in acetic acid.

The compounds of the general formulae II and III:

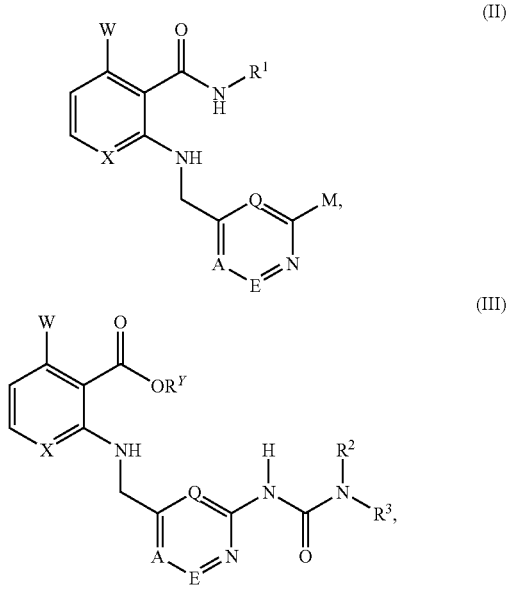

in which A, E, Q, W, $R^1$, $R^2$ and $R^3$, are defined in the same way as for the general formula (I), M is halogen and $R^y$ is H or $C_1$-$C_6$-alkyl, provide valuable intermediates for the preparation of the inventive compounds of general formula (I) and, are therefore also objects of the invention. The use of compounds of formula (II) and (III) in the production of a compound of formula (I), as well as the process described above using these compounds in the production of a compound of formula (I) are also objects of the invention.

EXAMPLES

Production of the Compounds According to the Invention

The following examples explain the production of the compounds according to the invention without the scope of the claimed compounds being limited to these examples.

Abbreviations

The following abbreviations used in the invention have the following meanings:
Brine saturated aqueous sodium chloride solution
CI+ chemical ionisation ($NH_3$)
DCE 1,2-dichloroethane
DMF N,N-dimethyl formamide
$d_6$-DMSO $d_6$-dimethylsulphoxide
d doublet
dd doublet of doublets
ES+ positive mode electrospray ionisation
EtOAc ethyl acetate
EtOH ethanol
1H-NMR proton nuclear magnetic resonance spectroscopy: chemical shifts (□) are given in ppm.
Hex n-hexane
LC-ES+ liquid chromatography/positive mode electrospray ionisation
LDA lithium diisopropylamide
MeOH methanol
m multiplet
Mp. melting point
MS mass spectrometry
m/z mass/charge ratio
$Pd_2dba_3$ tris-(dibenzylideneacetone)-dipalladium(0)-chloroform complex
rt room temperature
RT retention time (LC)
s singlet
THF tetrahydrofuran
t triplet
Xantphos 9,9-dimethyl-4,5-bis(diphenylphosphino)xanthene Example 1.0

Preparation of 4-hydroxy-4-methyl-piperidine-1-carboxylic acid (4-{[2-(2-methyl-2H-indazol-6-yl-carbamoyl)-phenylamino]-methyl}-pyridin-2-yl)-amide

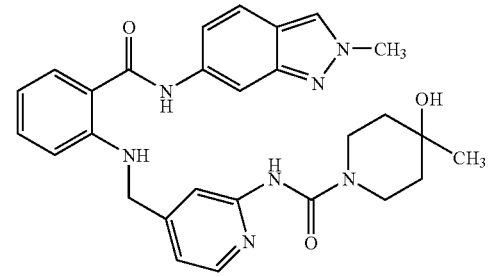

4-oxo-piperidine-1-carboxylic acid (4-{[2-(2-methyl-2H-indazol-6-ylcarbamoyl)-phenylamino]-methyl}-pyridin-2-yl)-amide (50 mg, 0.1 mmol) in dry THF under argon, at −78° C. was treated dropwise with methyllithium (1.5M in diethylether, 0.2 mL, 0.3 mmol). The reaction was stirred for 30 minutes at −78° C. before warming to rt. The reaction was stirred overnight before partitioning between EtOAc and saturated aqueous ammonium chloride solution. The organic phase was washed with brine, dried, filtered and concentrated in vacuo. The residue was purified by chromatography on Isolute® Flash silica gel (Separtis) (Gradient elution: 100% $CH_2Cl_2$ to $CH_2Cl_2$/EtOH 10:2) to give 4-hydroxy-4-methyl-piperidine-1-carboxylic acid (4-{[2-(2-methyl-2H-indazol-6-ylcarbamoyl)-phenylamino]-methyl}-pyridin-2-yl)-amide (12 mg, 23%) as a solid; 1H-NMR (300 MHz, $d_6$-DMSO) 10.13 (1H, s), 9.02 (1H, s), 8.25 (1H, s), 8.13 (1H, d), 8.10 (1H, s), 7.94 (1H, t), 7.80 (1H, s), 7.72 (1H, d), 7.64 (1H, d), 7.23-7.32 (2H, m), 6.92 (1H, d), 6.66 (1H, t), 6.54 (1H, d), 4.43 (2H, d), 4.31 (1H, s), 4.13 (3H, s), 3.68-3.74 (2H, m), 3.16-3.25 (2H, m), 1.35-1.46 (4H, m), 1.12 (3H, s); m/z (ES+) 514 $[M+H]^+$.

Example 1.1

Preparation of 4-hydroxy-piperidine-1-carboxylic acid (4-{[2-(2-methyl-2H-indazol-6-ylcarbamoyl)-phenylamino]-methyl}-pyridin-2-yl)-amide

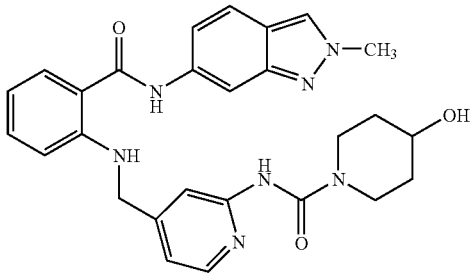

4-oxo-piperidine-1-carboxylic acid (4-{[2-(2-methyl-2H-indazol-6-ylcarbamoyl)-phenylamino]-methyl}-pyridin-2-yl)-amide (50 mg, 0.1 mmol) in absolute EtOH, at 4° C. was treated with sodium borohydride (4 mg, 0.1 mmol). The reaction was warmed to rt and stirred for 1 hour before the reaction was partitioned between EtOAc and water. The organic phase was washed with brine, dried, filtered and concentrated in vacuo to give 4-hydroxy-piperidine-1-carboxylic acid (4-{[2-(2-methyl-2H-indazol-6-ylcarbamoyl)-phenylamino]-methyl}-pyridin-2-yl)-amide (39 mg, 78%) as a solid; 1H-NMR (300 MHz, $d_6$-DMSO) 10.14 (1H, s), 9.07 (1H, s), 8.26 (1H, s), 8.14 (1H, d), 8.10 (1H, s), 7.94 (1H, t), 7.79 (1H, s), 7.71-7.73 (1H, m), 7.64 (1H, d), 7.30-7.33 (1H, m), 7.23-7.28 (1H, m), 6.92-6.94 (1H, m), 6.66 (1H, t), 6.54 (1H, d), 4.68 (1H, d), 4.43 (2H, d), 4.13 (3H, s), 3.79-3.84 (2H, m), 3.60-3.67 (1H, m), 3.00-3.08 (2H, m), 1.70-1.73 (2H, m), 1.23-1.35 (2H, m); m/z (ES+) 500 [M+H]+.

Example 1.2

Preparation of 4-hydroxy-4-trifluoromethyl-piperidine-1-carboxylic acid (4-{[2-(2-methyl-2H-indazol-6-ylcarbamoyl)-phenylamino]-methyl}-pyridin-2-yl)-amide

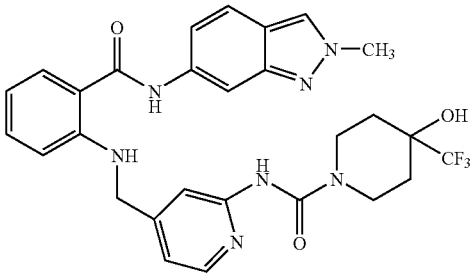

4-oxo-piperidine-1-carboxylic acid (4-{[2-(2-methyl-2H-indazol-6-ylcarbamoyl)-phenylamino]-methyl}-pyridin-2-yl)-amide (140 mg, 0.28 mmol) in dry THF was treated successively with trifluoromethyltrimethylsilane (0.06 mL, 0.42 mmol) and tetra-n-butylammonium fluoride (1M solution in THF, 0.28 mL, 0.28 mmol). The reaction was stirred at rt overnight before it was partitioned between EtOAc and water. The organic phase was washed with brine, dried, filtered and concentrated in vacuo. The residue was purified by chromatography on Isolute® Flash silica gel (Separtis) (Gradient elution: 100% $CH_2Cl_2$ to $CH_2Cl_2$/EtOH 10:1) to give 4-hydroxy-4-trifluoromethyl-piperidine-1-carboxylic acid (4-{[2-(2-methyl-2H-indazol-6-ylcarbamoyl)-phenylamino]-methyl}-pyridin-2-yl)-amide (15 mg, 9%) as a solid; 1H-NMR (300 MHz, $d_6$-DMSO) 10.14 (1H, s), 9.21 (1H, s), 8.25 (1H, s), 8.15 (1H, d), 8.10 (1H, s), 7.95 (1H, t), 7.80 (1H, s), 7.72 (1H, d), 7.63 (1H, d), 7.23-7.32 (2H, m), 6.94 (1H, d), 6.66 (1H, t), 6.53 (1H, d), 6.02 (1H, s), 4.44 (2H, d), 4.07-4.17 (5H, m), 2.95-3.05 (2H, m), 1.55-1.63 (4H, m); m/z (ES+) 568 [M+H]+.

Example 2.0

Preparation of 1-oxo-thiomorpholine-4-carboxylic acid (4-{[2-(2-methyl-2H-indazol-6-ylcarbamoyl)-phenylamino]-methyl}-pyridin-2-yl)-amide

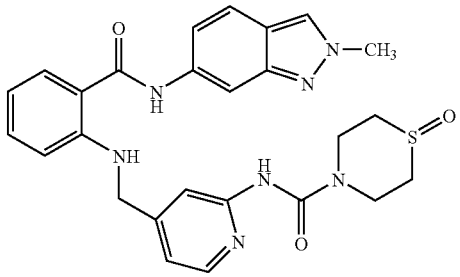

A mixture of thiomorpholine-4-carboxylic acid (4-{[2-(2-methyl-2H-indazol-6-ylcarbamoyl)-phenylamino]-methyl}-pyridin-2-yl)-amide (50 mg, 0.1 mmol) and sodium periodate (43 mg, 0.2 mmol) in MeOH/water (3:1, 4 mL) was stirred overnight at rt. The reaction was partitioned between EtOAc and brine and the organic phase dried, filtered and concentrated in vacuo to give 1-oxo-thiomorpholine-4-carboxylic acid (4-{[2-(2-methyl-2H-indazol-6-ylcarbamoyl)-phenylamino]-methyl}-pyridin-2-yl)-amide (30 mg, 58%) as a solid; 1H-NMR (300 MHz, $d_6$-DMSO) 10.14 (1H, s), 9.37 (1H, s), 8.25 (1H, s), 8.17 (1H, d), 8.10 (1H, s), 7.96 (1H, t), 7.82 (1H, s), 7.71-7.74 (1H, m), 7.63 (1H, d), 7.23-7.32 (2H, m), 6.96-6.98 (1H, m), 6.67 (1H, t), 6.54 (1H, d), 4.45 (2H, d), 4.13 (3H, s), 3.99-4.04 (2H, m), 3.66-3.74 (2H, m), 2.84-2.93 (2H, m), 2.65-2.70 (2H, m); m/z (LC-ES+) 518 [M+H]+.

Example 2.1

Preparation of 1,1-dioxo-thiomorpholine-4-carboxylic acid (4-{[2-(2-methyl-2H-indazol-6-ylcarbamoyl)-phenylamino]-methyl}-pyridin-2-yl)-amide

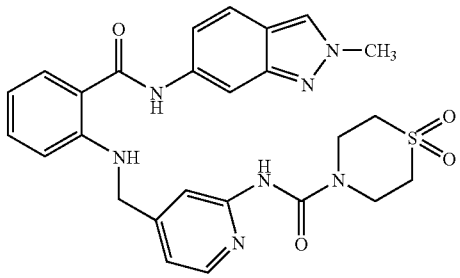

Thiomorpholine-4-carboxylic acid (4-{[2-(2-methyl-2H-indazol-6-ylcarbamoyl)-phenylamino]-methyl}-pyridin-2-yl)-amide (89 mg, 0.18 mmol) in acetone (6 mL) and distilled water (1.5 mL) was treated successively with 4-methylmorpholine-N-oxide (63 mg, 0.54 mmol) and osmiumtetraoxide (2.5% solution in water, 0.01 mL, catalytic). The reaction was stirred overnight before quenching with saturated aqueous sodium bisulfite solution. The mixture was extracted with $CH_2Cl_2$ and the organic phase was washed with water, dried, filtered and concentrated in vacuo to give 1,1-dioxo-thiomorpholine-4-carboxylic acid (4-{[2-(2-methyl-2H-indazol-6-ylcarbamoyl)-phenylamino]-methyl}-pyridin-2-yl)-amide (44 mg, 46%) as a solid; 1H-NMR (300 MHz, d₆-DMSO) 10.14 (1H, 5), 9.53 (1H, s), 8.25 (1H, s), 8.17 (1H, d), 8.10 (1H, s), 7.96 (1H, t), 7.81 (1H, 5), 7.71-7.73 (1H, m), 7.63 (1H, d), 7.23-7.32 (2H, m), 6.97-6.99 (1H, m), 6.67 (1H, t), 6.54 (1H, d), 4.45 (2H, d), 4.13 (3H, s), 3.87-3.90 (4H, m), 3.15-3.17 (4H, m); m/z (ES+) 534 [M+H]⁺.

Example 3.0

Preparation of 4-methyl-piperazine-1-carboxylic acid (4-{[2-(2-methyl-2H-indazol-6-ylcarbamoyl)-phenylamino]-methyl}-pyridin-2-yl)-amide

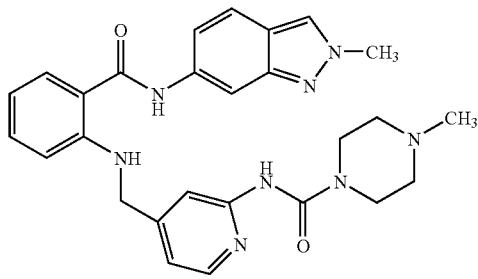

2-[(2-bromo-pyridin-4-ylmethyl)-amino]-N-(2-methyl-2H-indazol-6-yl)-benzamide (110 mg, 0.25 mmol) was suspended in dioxane (3 mL) and treated consecutively with DMF (1 mL), Pd₂dba₃ (5 mg, 0.005 mmol), Xantphos (9 mg, 0.015 mmol), cesium carbonate (98 mg, 0.3 mmol) and 4-methyl-piperazine-1-carboxylic acid amide (184 mg, 1.3 mmol). The reaction mixture was placed under a nitrogen atmosphere and heated for 3 hours at 110° C. (bath temperature). On cooling the volatiles were removed in vacuo and the residue was partitioned between CH₂Cl₂ and water. The organic phase was washed with brine, dried, filtered and concentrated. The residue was purified by chromatography using Isolute® Flash NH2 (Separtis) as stationary phase (Gradient elution: 100% CH₂Cl₂ to CH₂Cl₂/EtOH 95:5) to give 4-methyl-piperazine-1-carboxylic acid (4-{[2-(2-methyl-2H-indazol-6-ylcarbamoyl)-phenylamino]-methyl}-pyridin-2-yl)-amide (28 mg, 22%) as a foam; 1H-NMR (300 MHz, d₆-DMSO) 10.14 (1H, s), 9.11 (1H, s), 8.25 (1H, S), 8.14 (1H, d), 8.10 (1H, s), 7.95 (1H, t), 7.80 (1H, s), 7.72 (1H, d), 7.63 (1H, d), 7.23-7.32 (2H, m), 6.94 (1H, d), 6.66 (1H, t), 6.53 (1H, d), 4.43 (2H, d), 4.13 (3H, s), 3.41-3.44 (4H, m), 2.25-2.28 (4H, m), 2.17 (3H, s); m/z (ES+) 499.

The following compounds were prepared in analogy from the corresponding 2-bromopyridine intermediate and the corresponding urea intermediate:

| Example Nr. | *N(R²)(R³) | R¹ | MW | Mp. [° C.] or MS (m/z) |
|---|---|---|---|---|
| 3.1 | *N-piperazine-N-CH₃ | 1-methyl-1H-indazol-6-yl | 498.59 | Foam (ES+) 499 [M + H]⁺ |
| 3.2 | *N-piperazine-N-CH₂CH₂OH | 1-methyl-1H-indazol-6-yl | 528.61 | Foam (ES+) 529 [M + H]⁺ |
| 3.3 | *N-piperazine-N-CH₂CH₂OH | 2-methyl-2H-indazol-6-yl | 528.61 | Foam (ES+) 529 [M + H]⁺ |

-continued
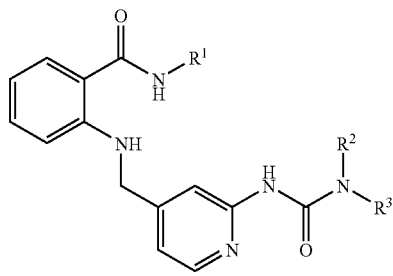
| Example Nr. |  $\overset{R^2}{\underset{R^3}{*N}}$ | R¹ | MW | Mp. [° C.] or MS (m/z) |
|---|---|---|---|---|
| 3.4 | 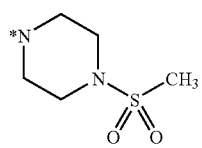 | 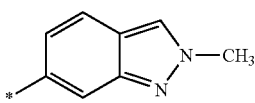 | 562.65 | Foam (ES+) 563 [M + H]⁺ |
| 3.5 | 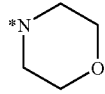 | 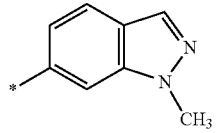 | 485.54 | Foam (ES+) 486 [M + H]⁺ |
| 3.6 | 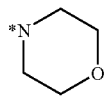 | 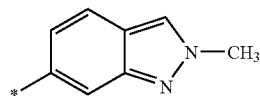 | 485.54 | Foam (ES+) 486 [M + H]⁺ |
| 3.7 | 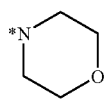 | 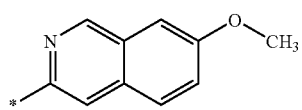 | 512.57 | Mp. 271 |
| 3.8 | 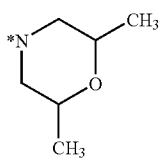 | 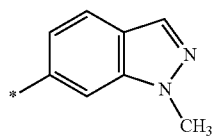 | 513.60 | Foam (ES+) 514 [M + H]⁺ |
| 3.9 | 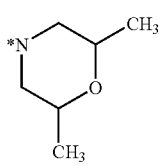 | 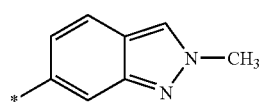 | 513.60 | Foam (ES+) 514 [M + H]⁺ |

Example 4.0

Preparation of 3-hydroxy-pyrrolidine-1-carboxylic acid (4-{[2-(2-methyl-2H-indazol-6-ylcarbamoyl)-phenylamino]-methyl}-pyridin-2-yl)-amide

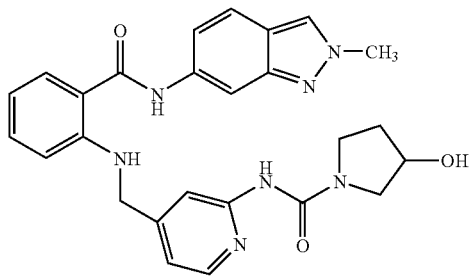

2-[(2-bromo-pyridin-4-ylmethyl)-amino]-N-(2-methyl-2H-indazol-6-yl)-benzamide (400 mg, 0.92 mmol) was suspended in dioxane (15 mL) and treated consecutively with DMF (5 mL), $Pd_2dba_3$ (19 mg, 0.02 mmol), Xantphos (32 mg, 0.06 mmol), cesium carbonate (358 mg, 1.1 mmol) and 3-hydroxy-pyrrolidine-1-carboxylic acid amide (358 mg, 2.75 mmol). The reaction mixture was placed under a nitrogen atmosphere and heated for 3 hours at 110° C. (bath temperature). On cooling the reaction was partitioned between EtOAc and water. The organic phase was washed with brine, dried, filtered and concentrated in vacuo. The residue was purified by chromatography on Isolute® Flash silica gel (Separtis) (Gradient elution: 100% $CH_2Cl_2$ to $CH_2Cl_2$/EtOH 10:1) to give 3-hydroxy-pyrrolidine-1-carboxylic acid (4-{[2-(2-methyl-2H-indazol-6-ylcarbamoyl)-phenylamino]-methyl}-pyridin-2-yl)-amide (270 mg, 61%) as a solid; 1H-NMR (300 MHz, $d_6$-DMSO) 10.14 (1H, s), 8.62 (1H, s), 8.25 (1H, s), 8.14 (1H, d), 8.10 (1H, s), 7.95 (1H, t), 7.90 (1H, s), 7.71-7.73 (1H, m), 7.64 (1H, d), 7.23-7.33 (2H, m), 6.93-6.95 (1H, m), 6.67 (1H, t), 6.53 (1H, d), 4.93 (1H, d), 4.43 (2H, d), 4.26 (1H, m), 4.13 (3H, s), 3.40-3.48 (4H, m), 1.79-1.94 (2H, m); m/z (ES+) 486 $[M+H]^+$.

Example 5.0

Preparation of morpholine-4-carboxylic acid (4-{[3-fluoro-2-(2-methyl-2H-indazol-6-ylcarbamoyl)-phenylamino]-methyl}-pyridin-2-yl)-amide

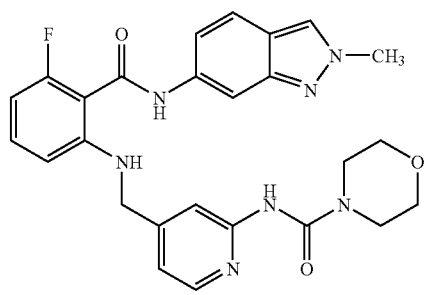

2-[(2-Bromo-pyridin-4-ylmethyl)-amino]-6-fluoro-N-(2-methyl-2H-indazol-6-yl)-benzamide (227 mg, 0.5 mmol) was suspended in dioxane (4 mL) and treated consecutively with DMF (1.6 mL), $Pd_2dba_3$ (13 mg, 0.013 mmol), Xantphos (18 mg, 0.031 mmol), cesium carbonate (193 mg, 0.59 mmol) and morpholine-4-carboxylic acid amide (244 mg, 0.75 mmol). The reaction mixture was placed under an argon atmosphere and heated for 3 hours at 110° C. (bath temperature). On cooling the reaction was partitioned between EtOAc and water. The organic phase was dried, filtered and concentrated in vacuo. The residue was purified by chromatography on Isolute® Flash silica gel (Separtis) (Gradient elution: 100% $CH_2Cl_2$ to $CH_2Cl_2$/EtOH 10:1) to give morpholine-4-carboxylic acid (4-{[3-fluoro-2-(2-methyl-2H-indazol-6-ylcarbamoyl)-phenylamino]-methyl}-pyridin-2-yl)-amide (132 mg, 52%) as a pale yellow resin. Further purification was accomplished by preparative reverse phase HPLC [Column: Kromasil C8 5μ, 125×20 mm. Eluant: 38% $CH_3CN$ in $H_2O$ (containing 0.2% $NH_3$) to 95% $CH_3CN$ in $H_2O$ (containing 0.2% $NH_3$)]; 1H-NMR (300 MHz, $d_6$-DMSO) 10.43 (1H, s), 9.15 (1H, s), 8.26 (1H, s), 8.23 (1H, s), 8.15 (1H, d), 7.79 (1H, s), 7.64 (1H, d), 7.13-7.25 (2H, m), -6.95 (1H, d), 6.73 (1H, t), 6.48 (1H, t), 6.29 (1H, d), 4.40 (2H, d), 4.14 (3H, s), 3.56-3.59 (4H, m), 3.42-3.45 (4H, m); m/z (ES+) 504 $[M+H]^+$.

Example 6.0

Preparation of morpholine-4-carboxylic acid (4-{[2-(isoquinolin-3-ylcarbamoyl)-phenylamino]-methyl}-pyridin-2-yl)-amide

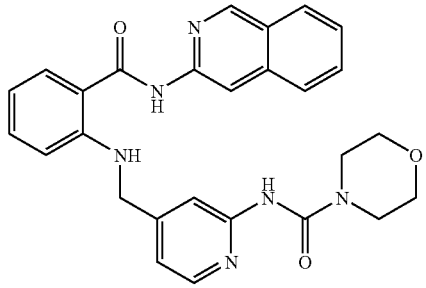

To a stirred solution of 3-aminoisoquinoline (75 mg, 0.52 mmol) and 2-({2-[(morpholine-4-carbonyl)-amino]-pyridin-4-ylmethyl}-amino)-benzoic acid methyl ester (149 mg, 0.40 mmol) in DCE (6 mL) at 0° C., under argon, was added trimethylaluminium (2M in toluene, 0.4 mL, 0.8 mmol). The reaction was heated at 120° C. (bath temperature) for 3 hours. On cooling the reaction was diluted with aqueous sodium hydrogencarbonate solution and extracted with dichloromethane. The organic phase was washed with water, dried and concentrated in vacuo. The residue was purified by chromatography on Isolute® flash NH2 (Separtis) (Eluant: EtOAc) to give morpholine-4-carboxylic acid (4-{[2-(isoquinolin-3-ylcarbamoyl)-phenylamino]-methyl}-pyridin-2-yl)-amide (60 mg, 32%) as a resin; 1H-NMR (300 MHz, $d_6$-DMSO) 10.69 (1H, s), 9.21 (1H, s), 9.18 (1H, s), 8.60 (1H, s), 8.16-8.20 (2H, m), 8.10 (1H, d), 7.96 (1H, d), 7.90 (1H, d), 7.82 (1H, d), 7.75 (1H, t), 7.57 (1H, t), 7.28 (1H, t), 6.98 (1H, d), 6.63 (1H, t), 6.58 (1H, d), 4.48 (2H, d), 3.55-3.59 (4H, m), 3.41-3.45 (4H, m); m/z (ES+) 483 $[M+H]^+$, 242.

The following compounds were prepared in analogy from 2-({2-[(morpholine-4-carbonyl)-amino]-pyridin-4-ylmethyl}-amino)-benzoic acid methyl ester and the corresponding amine:

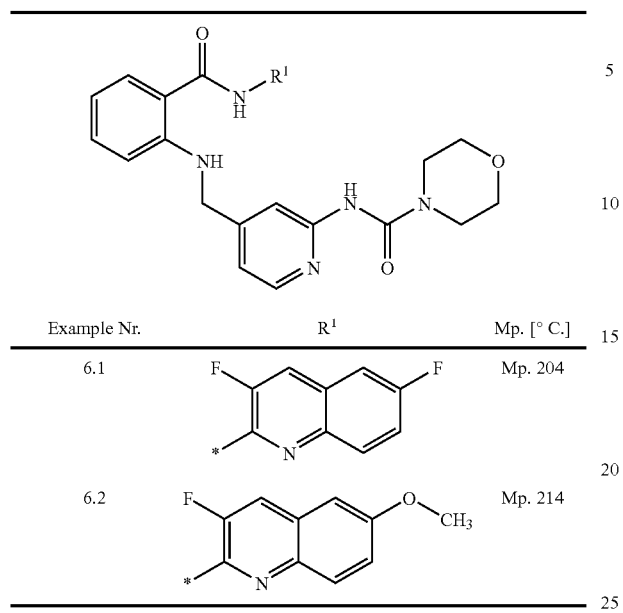

| Example Nr. | R¹ | Mp. [° C.] |
|---|---|---|
| 6.1 | (3,6-difluoroquinolin-2-yl) | Mp. 204 |
| 6.2 | (3-fluoro-6-methoxyquinolin-2-yl) | Mp. 214 |

Production of Starting and Intermediate Compounds

If the production of the intermediate compounds is not described, the latter are known or can be produced analogously to known compounds or processes that are described here or in WO2004/013102. Particularly, the intermediate compound 2-[(2-bromopyridin-4-yl-methyl)-amino]-N-(2-methyl-2H-indazol-6-yl)-benzamide is prepared as is published in WO 2004/013102, which is reiterated herein as Example 6A:

Example 6A

Step 1: Production of 2-[(2-Bromo-pyridin-4-ylmethyl)-amino]-benzoic Acid Methyl Ester

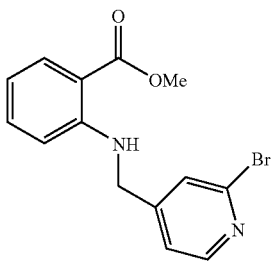

6.04 g (40 mmol) of anthranilic acid methyl ester in 600 ml of methanol is mixed with 3.2 ml of acetic acid and 7.4 g (40 mmol) of 2-bromopyridine-4-carbaldehyde and stirred overnight at 40° C. 3.8 g (60 mmol) of sodium cyanoborohydride is added thereto and stirred overnight at 40° C. 3.8 g (60 mmol) of sodium cyanoborohydride is added again and stirred over the weekend at 40° C. It is mixed with water and largely concentrated by evaporation. The aqueous phase is extracted with ethyl acetate, and the combined organic phases are dried, filtered and concentrated by evaporation. The crude product is chromatographed on silica gel with a gradient that consists of hexane and hexane/ethyl acetate 1:3 and hexane/ethyl acetate 1:1 as an eluant. 10.0 g (78% of theory) of 2-[(2-bromo-pyridin-4-ylmethyl)-amino]-benzoic acid methyl ester is obtained as a colorless oil.

Step 2: Production of 2-[(2-Bromo-pyridin-4-ylmethyl)-amino]-benzoic acid

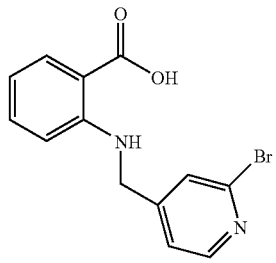

10.0 g (31.2 mmol) of 2-[(2-bromo-pyridin-4-ylmethyl)-amino]-benzoic acid methyl ester is dissolved in 290 ml of ethanol and mixed with 31.2 ml of 2 M sodium hydroxide solution. After having been stirred overnight at room temperature, the ethanol is drawn off, and the aqueous phase is shaken out with ethyl acetate. The aqueous phase is acidified with concentrated hydrochloric acid. The precipitate that is formed is suctioned off and dried. 5.93 g (62%) of 2-[(2-bromo-pyridin-4-ytmethyl)-amino]-benzoic acid accumulates in the form of a white solid.

Step 3: Production of 2-[(2-Bromo-pyridin-4-ylmethyl)-amino]-N-(2-methyl-2H-indazol-6-yl)-benzamide

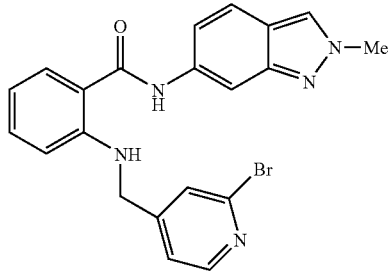

0.500 g (1.6 mmol) of 2-[(2-bromo-pyridin-4-ylmethyl)-amino]-benzoic acid, 0.471 g (3.2 mmol) of 2-methyl-2H-indazol-6-ylamine, 0.4 ml (3.68 mmol) of N-methylmorpholine and 0.729 g (1.92 mmol) of O-(7-azabenzotriazol-1-yl)-1,1,3,3-tetramethyluroniumhexafluorophosphate (HATU) in 25 ml of dimethylformamide are stirred for 16 hours at room temperature. The dimethylformamide is drawn off in an oil pump vacuum. The remaining residue is drawn off in saturated sodium bicarbonate solution it is extracted three times with ethyl acetate, and the combined organic phases are dried, filtered and concentrated by evaporation. The residue is chromatographed on silica gel with a gradient that consists of hexane:acetone=100:0 to 50:50 as an eluant. 0.669 g (96% of theory) of 2-[(2-bromo-pyridin-4-ylmethyt)-amino]-N-(2-methyl-2H-indazol-6-yl)-benzamide is obtained in the form of a beige foam.

Example 7.0

Preparation of 1,4-dioxa-8-aza-spiro[4.5]decane-8-carboxylic acid amide

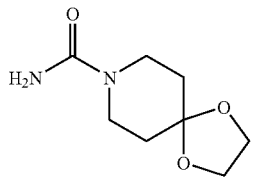

To a stirred solution of 1,4-dioxa-8-azaspiro[4,5]-decane (1.1 g, 7.67 mmol) in isopropanol (20 mL) at rt was added trimethylsilylisocyanate (1.5 mL, 10.6 mmol) and the resulting solution stirred overnight before the volatiles were removed in vacuo to give 1,4-dioxa-8-aza-spiro[4.5]decane-8-carboxylic acid amide (1.47 g, quant.); 1H-NMR (300 MHz, $d_6$-DMSO) 5.96 (2H, s), 3.88 (4H, s), 3.33 (4H, t), 1.51 (4H, t).

Example 7.1

Preparation of 1,4-dioxa-8-aza-spiro[4.5]decane-8-carboxylic acid (4-{[2-(2-methyl-2H-indazol-6-ylcarbamoyl)-phenylamino]-methyl}-pyridin-2-yl)-amide

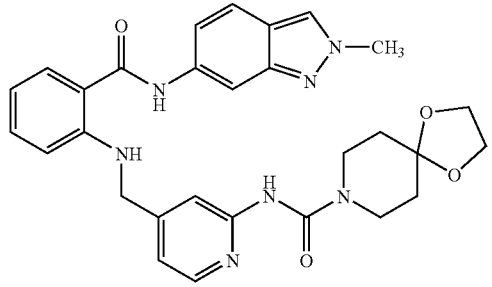

2-[(2-bromo-pyridin-4-ylmethyl)-amino]-N-(2-methyl-2H-indazol-6-yl)-benzamide (700 mg, 1.6 mmol) was suspended in dioxane (26 mL) and treated consecutively with DMF (7 mL), $Pd_2dba_3$ (32 mg, 0.03 mmol), Xantphos (61 mg, 0.1 mmol), cesium carbonate (632 mg, 1.9 mmol) and 1,4-dioxa-8-aza-spiro[4.5]decane-8-carboxylic acid amide (930 mg, 5 mmol). The reaction mixture was placed under a nitrogen atmosphere and heated for 4 hours at 110° C. (bath temperature). On cooling the reaction was partitioned between EtOAc and brine. The organic phase was dried, filtered and concentrated in vacuo. The residue was purified by chromatography on Isolute® Flash silica gel (Separtis) (Gradient elution: 100% $CH_2Cl_2$ to $CH_2Cl_2$/EtOH 10:1) to give 1,4-dioxa-8-aza-spiro[4.5]decan-8-carboxylic acid(4-{[2-(2-methyl-2H-indazol-6-ylcarbamoyl)-phenylamino]-methyl}-pyridin-2-yl)-amide (574 mg, 66%) as a solid; 1H-NMR (300 MHz, $d_6$-DMSO) 10.20 (1H, s), 9.25 (1H, s), 8.32 (1H, s), 8.21 (1H, d), 8.17 (1H, s), 8.01 (1H, t), 7.87 (1H, s), 7.75-7.80 (1H, m), 7.70 (1H, d), 7.30-7.40 (2H, m), 6.99-7.01 (1H, m), 6.73 (1H, t), 6.60 (1H, d), 4.50 (2H, d), 4.20 (3H, s), 3.97 (4H, s), 3.54-3.59 (4H, m), 1.53-1.58 (4H, m); m/z (ES+) 542 [M+H]+.

Example 7.2

Preparation of 4-oxo-piperidine-1-carboxylic acid (4-{[2-(2-methyl-2H-indazol-6-ylcarbamoyl)-phenylamino]-methyl}-pyridin-2-yl)-amide

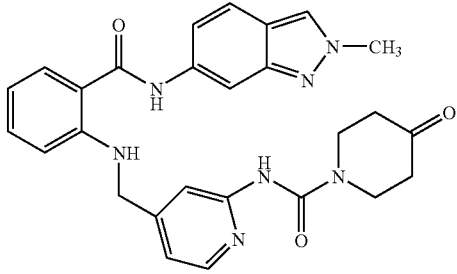

1,4-Dioxa-8-aza-spiro[4.5]decan-8-carboxylic acid(4-{[2-(2-methyl-2H-indazol-6-ylcarbamoyl)-phenylamino]-methyl}-pyridin-2-yl)-amide (564 mg, 1.04 mmol) in acetone (35 mL), was cooled to 4° C. and treated dropwise with aqueous hydrochloric acid (4 N, 9 mL). The reaction was warmed to rt and stirred overnight. The reaction was made basic by the addition of saturated aqueous sodium hydrogencarbonate and extracted with EtOAc. The organic phase was washed with brine, dried, filtered and concentrated in vacuo to give 4-oxo-piperidine-1-carboxylic acid (4-{[2-(2-methyl-2H-indazol-6-ylcarbamoyl)-phenylamino]-methyl}-pyridin-2-yl)-amide (467 mg, 90%) as a solid; 1H-NMR (300 MHz, $d_6$-DMSO) 10.14 (1H, s), 9.36 (1H, s), 8.25 (1H, s), 8.17 (1H, d), 8.10 (1H, s), 7.96 (1H, t), 7.86 (1H, s), 7.72 (1H, d), 7.64 (1H, d), 7.23-7.32 (2H, m), 6.96-6.98 (1H, m), 6.66 (1H, t), 6.55 (1H, d), 4.45 (2H, d), 4.13 (3H, s), 3.72-3.76 (4H, m), 2.36-2.40 (4H, m); m/z (ES+) 498 [M+H]+.

Example 8.0

Preparation of thiomorpholine-4-carboxylic acid amide

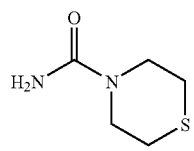

To a stirred solution of thiomorpholine (1.0 g, 9.7 mmol) in isopropanol (25 mL) at rt was added trimethylsilylisocyanate (1.9 mL, 13.45 mmol) and the resulting solution stirred overnight. The resulting suspension was filtered and the filtrate concentrated in vacuo to give thiomorpholine-4-carboxylic acid amide (1.18 g, 89%); 1H-NMR (300 MHz, $d_6$-DMSO) 6.00 (2H, s), 3.53-3.57 (4H, m), 2.46-2.51 (4H, m, obscured by solvent).

Example 8.1

Preparation of thiomorpholine-4-carboxylic acid (4-{[2-(2-methyl-2H-indazol-6-ylcarbamoyl)-phenylamino]-methyl}-pyridin-2-yl)-amide

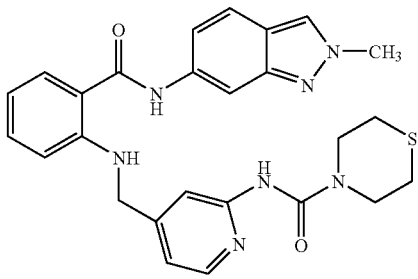

2-[(2-bromo-pyridin-4-ylmethyl)-amino]-N-(2-methyl-2H-indazol-6-yl)-benzamide (500 mg, 1.15 mmol) was suspended in dioxane (14 mL) and treated consecutively with DMF (5 mL), $Pd_2dba_3$ (23 mg, 0.023 mmol), Xantphos (42 mg, 0.07 mmol), cesium carbonate (454 mg, 1.38 mmol) and thiomorpholine-4-carboxylic acid amide (511 mg, 3.5 mmol). The reaction mixture was placed under a nitrogen atmosphere and heated for 4 hours at 110° C. (bath temperature). On cooling the reaction was partitioned between EtOAc and water. The organic phase was washed with brine, dried, filtered and concentrated in vacuo. The residue was purified by chromatography on Isolute® Flash silica gel (Separtis) (Gradient elution: 100% $CH_2Cl_2$ to $CH_2Cl_2$/EtOH 10:1) to give thiomorpholine-4-carboxylic acid (4-{[2-(2-methyl-2H-indazol-6-ylcarbamoyl)-phenylamino]-methyl}-pyridin-2-yl)-amide (375 mg, 65%) as a solid; 1H-NMR (300 MHz, $d_6$-DMSO) 10.14 (1H, s), 9.20 (1H, s), 8.25 (1H, s), 8.15 (1H, d), 8.11 (1H, s), 7.95 (1H, t), 7.80 (1H, s), 7.72 (1H, d), 7.63 (1H, d), 7.23-7.33 (2H, m), 6.95 (1H, d), 6.67 (1H, t), 6.54 (1H, d), 4.44 (2H, d), 4.13 (3H, s), 3.70-3.73 (4H, m), 2.55-2.58 (4H, m); m/z (ES+) 502 $[M+H]^+$.

Example 9.0

Preparation of 4-methyl-piperazine-1-carboxylic acid amide

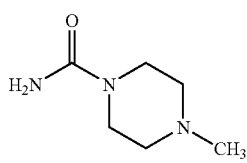

To a stirred solution of 1-methylpiperazine (1.66 mL, 15 mmol) in isopropanol (30 mL) at rt was added trimethylsilylisocyanate (2.8 mL, 21 mmol) and the resulting solution stirred overnight. The volatiles were removed in vacuo to give 4-methyl-piperazine-1-carboxylic acid amide (2.6 g, quant.) as an oil which slowly crystallised on standing; 1H-NMR (300 MHz, $CDCl_3$) 4.62 (2H, s), 3.40 (4H, t), 2.39 (4H, t), 2.29 (3H, s); m/z (ES+) 143 $[M+H]^+$.

Example 10.0

Preparation of 4-(2-hydroxy-ethyl)-piperazine-1-carboxylic acid amide

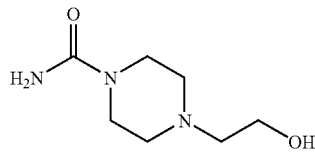

To a stirred solution of 1-(2-hydroxy-ethyl)-piperazine (1.95 g, 15 mmol) in isopropanol (30 mL) at rt was added trimethylsilylisocyanate (2.8 mL, 21 mmol) and the resulting solution stirred overnight before the volatiles were removed in vacuo. The residue was partitioned between $CH_2Cl_2$ and water. The aqueous phase was concentrated in vacuo to give 4-(2-hydroxy-ethyl)-piperazine-1-carboxylic acid amide (2.3 g, 88%); 1H-NMR (300 MHz, $d_6$-DMSO) 5.92 (2H, s), 4.40 (1H, t), 3.46-3.52 (2H, m), 3.22-3.34 (4H, m), 2.30-2.39 (6H, m); m/z (ES+) 173 $[M+H]^+$.

Example 11.0

Preparation of 4-methanesulfonyl-piperazine-1-carboxylic acid amide

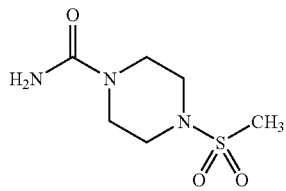

To a stirred suspension of N-methanesutfonylpiperazine (1.0 g, 6.1 mmol) in isopropanol (15 mL) at rt was added trimethylsilylisocyanate (1.4 mL, 11 mmol) and the resulting suspension stirred overnight before the precipitate was filtered and dried to give 4-methanesulfonyl-piperazine-1-carboxylic acid amide (1.35 g, quant.) as a solid; 1H-NMR (300 MHz, $d_6$-DMSO) 6.10 (2H, s), 3.37-3.40 (4H, m), 3.03-3.06 (4H, m), 2.90 (3H, s).

Example 12.0

Preparation of morpholine-4-carboxylic acid amide

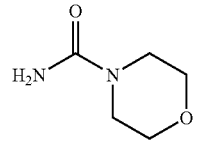

To a stirred solution of morpholine (1.3 mL, 15 mmol) in isopropanol (30 mL) at rt was added trimethylsilylisocyanate (2.8 mL, 21 mmol) and the resulting solution stirred overnight before the volatiles were removed in vacuo to give morpholine-4-carboxylic acid amide (2.0 g, quant.) as a solid; 1H-NMR (300 MHz, $d_6$-DMSO) 6.00 (2H, s), 3.51-3.54 (4H, s), 3.23-3.26 (4H, s).

Example 13.0

Preparation of
2,6-dimethyl-morpholine-4-carboxylic acid amide

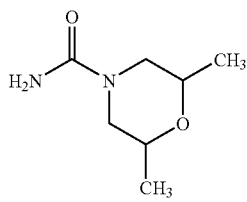

To a stirred solution of 2,6-dimethylmorpholine (mixture of cis- and trans-isomers, 1.7 g, 15 mmol) in isopropanol (30 mL) at rt was added trimethylsilylisocyanate (2.8 mL, 21 mmol) and the resulting solution stirred overnight before the volatiles were removed in vacuo to give a mixture of cis- and trans-2,6-dimethyl-morpholine-4-carboxylic acid amide (2.7 g, quant.) as a solid; m/z (ES+) 158 [M+H]$^+$.

Example 14.0

Preparation of 3-hydroxy-pyrrolidine-1-carboxylic acid amide

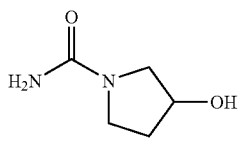

To a stirred solution of 3-hydroxypyrrolidine (1.0 g, 11.48 mmol) in isopropanol (27 mL) at rt was added trimethylsilyl-isocyanate (2.14 mL, 16.07 mmol) and the resulting solution stirred overnight. The resulting suspension was filtered and the residue washed with isopropanol and dried to give 3-hydroxy-pyrrolidine-1-carboxylic acid amide (0.89 g, 60%); 1H-NMR (300 MHz, d$_6$-DMSO) 5.64 (2H, s), 4.85 (1H, d), 4.21-4.22 (1H, m), 3.22-3.28 (3H, m), 3.06-3.10 (1H, m), 1.79-1.90 (1H, m), 1.67-1.76 (1H, m).

Example 15.0

Preparation of 2-[(2-bromo-pyridin-4-ylmethyl)-amino]-N-(7-methoxy-isoquinolin-3-yl)-benzamide

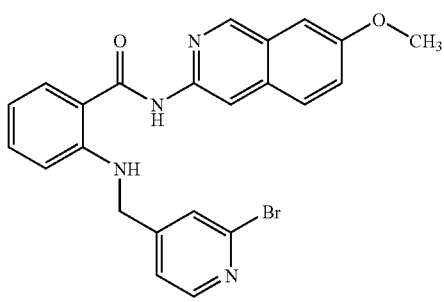

2-[(2-Bromo-pyridin-4-ylmethyl)-amino]-N-(7-methoxy-isoquinolin-3-yl)benzamide was prepared from 2-[(2-bromo-pyridin-4-ylmethyl)-amino]-benzoic acid methyl ester and 3-amino-7-methoxyisoquinoline in analogy to the procedures detailed in WO2004/013102, particularly Example 6A; supra; 1H-NMR (300 MHz, d$_6$-DMSO) 10.62 (1H, s), 9.10 (1H, s), 8.51 (1H, s), 8.32 (1H, d), 8.11 (1H, t), 7.83-7.90 (2H, m), 7.60 (1H, s), 7.50 (1H, m), 7.38-7.41 (2H, m), 7.27 (1H, t), 6.66 (1H, t), 6.55 (1H, d), 4.54 (2H, d), 3.91 (3H, s).

Example 16.0

Preparation of 2-[(2-bromo-pyridin-4-ylmethyl)-amino]-6-fluoro-N-(2-methyl-2H-indazol-6-yl)-benzamide

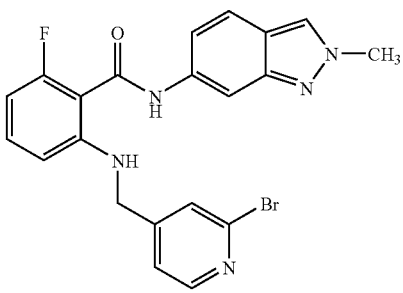

2-[(2-Bromo-pyridin-4-ylmethyl)-amino]-6-fluoro-N-(2-methyl-2H-indazol-6-yl)-benzamide was prepared from methyl 2-amino-6-fluorobenzoate via reductive amination with 2-bromo-pyridine-4-carbaldehyde, followed by subsequent amidation with 6-amino-2-methyl-indazole in analogy to the procedures detailed in WO2004/013102, particularly Example 6A, supra; 1H-NMR (300 MHz, d$_6$-DMSO) 10.51 (1H, s), 8.31 (1H, d), 8.26-8.28 (2H, m), 7.65 (1H, d), 7.59 (1H, s), 7.40 (1H, d), 7.13-7.25 (2H, m), 6.73 (1H, t), 6.50 (1H, t), 6.29 (1H, d), 4.47 (2H, d), 4.13 (3H, s).

Example 17.0

Preparation of 2-({2-[(morpholine-4-carbonyl)-amino]-pyridin-4-ylmethyl}-amino)-benzoic acid methyl ester

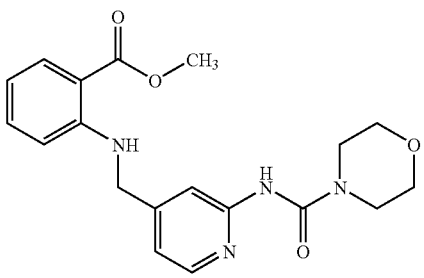

2-({2-[(Morpholine-4-carbonyl)-amino]-pyridin-4-ylmethyl}-amino)-benzoic acid methyl ester was prepared from 2-[(2-bromo-pyridin-4-ylmethyl)-amino]-benzoic acid methyl ester and morpholine-4-carboxylic acid amide in analogy to the procedures detailed in WO2004/013102, particularly Example 6A, supra; 1H-NMR (300 MHz, d$_6$-DMSO) 9.19 (1H, s), 8.15-8.19 (2H, m), 7.79-7.84 (2H, m), 7.29-7.34 (1H, m), 6.92 (1H, dd), 6.56-6.62 (2H, m), 4.50 (2H, d), 3.83 (3H, s), 3.57-3.60 (4H, m), 3.42-3.46 (4H, m).

The following examples detail the biological activity and use of the compounds of the invention without the scope of the claimed compounds being limited to these examples.

KDR Kinase Inhibition

Kinase activity was measured with a GST-kinase domain fusion construct of the KDR kinase according to the following protocol to obtain concentration response curves. Components were added into a microtiterplate in the following sequence: 10 µl of inhibitor in threefold final concentration [3% DMSO in buffer (40 mM TrisCl pH 7.5; 1 mM DTT, 1 mM MnCl$_2$, 10 mM MgCl$_2$, 2.5 Promille Polyethyleneglycol 20000)]and 10 µl of substrate mixture [24 µM ATP, 24 µg/ml poly(Glu$_4$Tyr) in buffer, specific activity approx. 500 cpm/pmol $^{32}$P-☐ATP]. Reaction was started by adding 10 µl of enzyme preparation diluted appropriately in buffer that contains 10 µM vanadate. After incubation for exactly 10 min the reaction was stopped by adding of 10 µl stop solution (250 mM EDTA). 10 µl of the reaction mixture were transferred to phosphocellulose filters. The filters were washed in 0.1% phosphoric acid, dried before meltilex scintillator was applied (Waltac, Perkin-Elmer) and the radioactivity was counted.

VEGFR-3 Autophosphorylation

MVECs (1.5×10$^6$/well) of a low passage number were plated on collagen-G coated 48 well plates in EBM complete medium (including EGM-2, BD-Clonetech). 5 h later, medium was exchanged for EBM-2 without EGM-2 but containing 0.2% BSA (EBM meager). 12 h later medium was removed, 250 µl EBM-2 meager and the respective compound dilutions were added in 50 µl EBM-2 meager. Solutions were carefully mixed and left for 5 min at 4° C. before the addition of 200 µl EBM-2 meager containing VEGF-C (final concentration in the assay is 5 nM; Reliatech, Braunschweig). The solution was then carefully mixed and incubated for 15 min at room temperature. The medium was removed and cells were washed twice with cold PBS/2 mM vanadate. Cells were then lysed with 100 µl Duschl buffer [50 mM Hepes pH 7.2; 150 mM NaCl; 1 mM MgCl$_2$; 1.5% Triton X-100; 10 mM Na-Pyrophosphate; 100 mM Na-Fluoride; 10% glycerol+(freshly added before the experiment) 2 mM Orthovanadate and 1 tablet per 50 ml Complete (Roche # 1836145)]

For the ELISA, Fluoronic MaxiSorp—MTP plates (# 3204006 Zinser)—were coated overnight at 4° C. with Flt-4 antibody (Flt-4 (C-20) # sc-321 Santa Cruz); 1 µg/ml in coating buffer: Na$_2$CO$_3$ pH 9.6 100 µl/well). After 3× washing with washing buffer (0.1% Tween 20 in Na$_2$HPO$_4$ pH 7.4) the wells were incubated with 250 µl blocking buffer (Roti Block $^1$/$_{10}$ from Roth, Karlsruhe for 1 h at room temperature). 3× washing with washing buffer was followed-by addition of cell lysates and incubation over night at 4° C. Then wells were washed 3×, anti-phosophotyrosine antibody coupled to HRP (16-105; UPSTATE; dilution 1/20000 in TBST+3% Top Block # 37766, Fluka) was added and incubated overnight at 4° C. Washing with washing buffer (6×) preceded the addition of BM chemoluminescence ELISA reagent # 1582950 (Roche) and measurement of luminescence.

Cytochrome P450 Inhibition

The Cytochrome P450 isoenzyme inhibition was performed according to the publication of Crespi et al. (Anal. Biochem., 1997, 248, 188-190) with use of the baculovirus/insect cell-expressed, human Cytochrome P 450 isoenzymes (2C9 and 2C19).

Selected results are presented in the following table:

| Example | IC50 KDR-Kinase (VEGFR-2) (nM) | IC50 CYP 2C9 (µM) | IC50 CYP 2C19 (µM) |
|---|---|---|---|
| 3.30 from WO 04/13102 | 10 | 0.9 | 1.7 |
| 3.40 from WO 04/13102 | 40 | 1.1 | 2.3 |
| 3.41 from WO 04/13102 | 27 | 5.7 | 1.5 |
| 1.1 | 20 | 16.0 | 27.0 |
| 1.2 | 17 | 19.0 | 12.0 |
| 3.0 | 29 | 4.4 | 8.9 |
| 3.6 | 29 | 13.0 | 9.0 |

The advantages of the compounds of the invention compared to known compounds can be readily demonstrated by the above studies.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 04090418.7, filed Nov. 3, 2004 and U.S. Provisional Application Ser. No. 60/626,919, filed Nov. 12, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I):

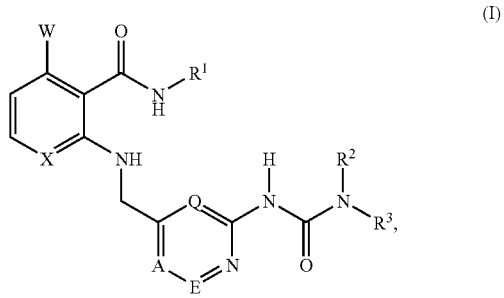

wherein:
x is CH;
W is hydrogen or fluorine;
A, E and Q independently of one another, are CH or N, wherein only a maximum of two nitrogen atoms are contained in the ring;
R$^1$ is aryl or heteroaryl, which is optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$;

$R^2$ and $R^3$ together with the nitrogen atom to which they are attached form a 3-8 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, wherein $C_1$-$C_{12}$ alkyl is optionally substituted with a group —$OR^5$;

$R^4$ is $C_1$-$C_{12}$-alkyl, $C_3$-$C_8$-cycloalkyl, aryl or heteroaryl;

$R^5$ is hydrogen, $C_1$-$C_{12}$-alkyl, $C_3$-$C_8$-cycloalkyl or halo-$C_1$-$C_6$-alkyl;

$R^6$ is hydrogen, $C_1$-$C_{12}$-alkyl, $C_3$-$C_8$-cycloalkyl, halo-$C_1$-$C_6$-alkyl, aryl or —$NR^7R^8$;

$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —$OR^5$ or —$N(CH_3)_2$, or $R^7$ and $R^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —$OR^5$, —$COR^6$, —$SR^4$, —$SOR^4$ or —$SO_2R^6$;

or a diastereoisomer, enantiomer, tautomer or salt thereof.

2. A compound as claimed in claim 1, wherein W is hydrogen.

3. A compound as claimed in claim 1, wherein A, E, and Q each Are CH.

4. A compound as claimed in claim 1, wherein W is hydrogen, and A, E, and Q each are CH.

5. A compound as claimed in claim 1, wherein $R^1$ is heteroaryl optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$.

6. A compound as claimed in claim 1, wherein $R^1$ is heteroaryl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$.

7. A compound as claimed in claim 1, wherein $R^1$ is quinolinyl, isoquinolinyl, or indazolyl which is optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$, alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$.

8. A compound as claimed in claim 1, wherein $R^1$ is quinolinyl, isoquinolinyl, or indazolyl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$.

9. A compound as claimed in claim 1, wherein $R^1$ is indazolyl substituted with $C_1$-$C_{12}$-alkyl.

10. A compound as claimed in claim 1, wherein $R^1$ is 2-methyl-indazolyl or 1-methyl-indazolyl.

11. A compound as claimed in claim 1, wherein $R^2$ and $R^3$ together with the nitrogen atom to which they are attached form a 5 or 6 membered heterocycloalkyl ring, which contains no or at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$, or —$CO_2R_6$, wherein $C_1$-$C_{12}$ alkyl is optionally substituted with a group —$OR^5$.

12. A compound as claimed in claim 1, wherein $R^4$ is $C_1$-$C_{12}$-alkyl.

13. A compound as claimed in claim 1, wherein $R^4$ is —$CH_3$.

14. A compound as claimed in claim 1, wherein $R^5$ is —$CH_3$ or hydrogen.

15. A compound as claimed in claim 1, wherein $R^5$ is hydrogen.

16. A compound as claimed in claim 1, wherein $R^6$ is $C_1$-$C_{12}$-alkyl or —$NR^7R^8$.

17. A compound as claimed in claim 1, wherein $R^6$ is $C_1$-$C_{12}$-alkyl.

18. A compound as claimed in claim 1, wherein $R^6$ is —$CH_3$.

19. A compound as claimed in claim 1, wherein $R^7$ and $R^8$ independently of one another, are hydrogen, —$COR^6$, —$SO_2R^6$, or $C_1$-$C_{12}$-alkyl.

20. A compound as claimed in claim 1, wherein $R^7$ and $R^8$ independently of one another, are hydrogen or —$CH_3$.

21. A compound as claimed in claim 1,
wherein:

W is hydrogen;

A, E and Q each are CH;

$R^1$ is aryl or heteroaryl, which is optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$;

$R^2$ and $R^3$ together with the nitrogen atom to which they are attached form a 3-8 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, wherein $C_1$-$C_{12}$ alkyl is optionally substituted with a group —$OR^5$;

$R^4$ is $C_1$-$C_{12}$-alkyl, $C_3$-$C_8$-cycloalkyl, aryl or heteroaryl;

$R^5$ is hydrogen, $C_1$-$C_{12}$-alkyl, $C_3$-$C_8$-cycloalkyl or halo-$C_1$-$C_6$-alkyl;

$R^6$ is hydrogen, $C_1$-$C_{12}$-alkyl, $C_3$-$C_8$-cycloalkyl, halo-$C_1$-$C_6$-alkyl, aryl or $NR^7R^8$;

$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —$OR^5$ or —$N(CH_3)_2$, or $R^7$ and $R^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, —COR$^6$, —SR$^4$, —SOR$^4$ or —SO$_2$R$^6$;

or a diastereoisomer, enantiomer, tautomer or salt thereof.

22. A compound as claimed in claim 1,
wherein:
W is hydrogen;
A, E and Q each are CH;
R$^1$ heteroaryl substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, wherein $C_1$-$C_{12}$-alkyl may be substituted with —NR$^7$R$^8$;
R$^2$ and R$^3$ together with the nitrogen atom to which they are attached form a 3-8 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR$^5$, —SR$^4$, —SOR$^4$, —SO$_2$R$^6$, —COR$^6$ or —CO$_2$R$^6$, wherein $C_1$-$C_{12}$ alkyl is optionally substituted with a group —OR$^5$;
R$^4$ is $C_1$-$C_{12}$-alkyl, $C_3$-$C_8$-cycloalkyl, aryl or heteroaryl;
R$^5$ is hydrogen, $C_1$-$C_{12}$-alkyl, $C_3$-$C_8$-cycloalkyl or halo-$C_1$-$C_6$-alkyl;
R$^6$ is hydrogen, $C_1$-$C_{12}$-alkyl, $C_3$-$C_8$-cycloalkyl, halo-$C_1$-$C_6$-alkyl, aryl or —NR$^7$R$^8$;
R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_2$-alkyl is optionally substituted with —OR$^5$ or —N(CH$_3$)$_2$, or
R$^7$ and R$^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, —COR$^6$, —SR$^4$, —SOR$^4$ or —SO$_2$R$^6$;

or a diastereoisomer, enantiomer, tautomer or salt thereof.

23. A compound as claimed in claim 1, wherein:
W is hydrogen;
A, E and Q each are CH;
R$^1$ is quinolinyl, isoquinolinyl, or indazolyl which is optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, wherein $C_1$-$C_{12}$-alkyl may be substituted with —NR$^7$R$^8$;
R$^2$ and R$^3$ together with the nitrogen atom to which they are attached form a 3-8 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR$^5$, —SR$^4$, —SOR$^4$, —SO$_2$R$^6$, —COR$^6$ or —CO$_2$R$^6$, wherein $C_1$-$C_{12}$ alkyl is optionally substituted with a group —OR$^5$;
R$^4$ is $C_1$-$C_{12}$-alkyl, $C_3$-$C_8$-cycloalkyl, aryl or heteroaryl;
R$^5$ is hydrogen, $C_1$-$C_2$-alkyl, $C_3$-$C_8$-cycloalkyl or halo-$C_1$-$C_6$-alkyl;
R$^6$ is hydrogen, $C_1$-$C_{12}$-alkyl, $C_3$-$C_8$-cycloalkyl, halo-$C_1$-$C_6$-alkyl, aryl or —NR$^7$R$^8$;
R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —OR$^5$ or —N(CH$_3$)$_2$, or
R$^7$ and R$^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, —COR$^6$, —SR$^4$, —SOR$^4$ or —SO$_2$R$^6$;

or a diastereoisomer, enantiomer, tautomer or salt thereof.

24. A compound as claimed in claim 1, wherein:
W is hydrogen;
A, E and Q each are CH;
R$^1$ is quinolinyl, isoquinolinyl, or indazolyl which is substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, wherein $C_1$-$C_{12}$-alkyl may be substituted with —NR$^7$R$^8$;
R$^2$ and R$^3$ together with the nitrogen atom to which they are attached form a 5 or 6 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl $C_1$-$C_3$-dialkyl ketal, $C_1$-$C_3$-cyclic ketal, =O, —OR$^5$, —SR$^4$, —SOR$^4$, —SO$_2$R$^6$, —COR$^6$ or —CO$_2$R$^6$, wherein $C_1$-$C_{12}$ alkyl is optionally substituted with a group —OR$^5$;
R$^4$ is $C_1$-$C_{12}$-alkyl, $C_3$-$C_8$-cycloalkyl, aryl or heteroaryl;
R$^5$ is hydrogen, $C_1$-$C_{12}$-alkyl, $C_3$-$C_8$-cycloalkyl or halo-$C_1$-$C_6$-alkyl;
R$^6$ is hydrogen, $C_1$-$C_{12}$-alkyl, $C_3$-$C_8$-cycloalkyl, halo-$C_1$-$C_6$-alkyl, aryl or —NR$^7$R$^8$;
R$^7$ and R$^8$ independently of one another, are hydrogen, —SO$_2$R$^6$, —COR$^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —OR$^5$ or —N(CH$_3$)$_2$, or
R$^7$ and R$^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR$^5$, —COR$^6$, —SR$^4$, —SOR$^4$ or —SO$_2$R$^6$;

or a diastereoisomer, enantiomer, tautomer or salt thereof.

25. A compound as claimed in claim 1,
wherein:
W is hydrogen;
A, E and Q each are CH;
R$^1$ is indazolyl which is optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —SO$_2$R$^6$, —OR$^5$, —SOR$^4$, —COR$^6$, —CO$_2$R$^6$ or —NR$^7$R$^8$, wherein $C_1$-$C_{12}$-alkyl may be substituted with —NR$^7$R$^8$;
R$^2$ and R$^3$ together with the nitrogen atom to which they are attached form a 5 or 6 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —OR$^5$, —SOR$^4$, —SO$_2$R$^6$, —COR$^6$ or —CO$_2$R$^6$, wherein $C_1$-$C_{12}$ alkyl is optionally substituted with a group —OR$^5$;

$R^4$ is $C_1$-$C_{12}$-alkyl, $C_3$-$C_8$-cycloalkyl, aryl or heteroaryl;
$R^5$ is hydrogen, $C_1$-$C_{12}$-alkyl, $C_3$-$C_8$-cycloalkyl or halo-$C_1$-$C_6$-alkyl;
$R^6$ is hydrogen, $C_1$-$C_{12}$-alkyl, $C_3$-$C_8$-cycloalkyl, halo-$C_1$-$C_6$-alkyl, aryl or $NR^7R^8$;
$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —$OR^5$ or —$N(CH_3)_2$, or
$R^7$ and $R^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —$OR^5$, —$COR^6$, —$SR^4$, —$SOR^4$ or —$SO_2R^6$;

or a diastereoisomer, enantiomer, tautomer or salt thereof.

26. A compound as claimed in claim 1,
wherein:
W is hydrogen;
A, E and Q each are CH;
$R^1$ is indazolyl substituted with $C_1$-$C_{12}$-alkyl;
$R^2$ and $R^3$ together with the nitrogen atom to which they are attached form a 5 or 6 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, wherein $C_1$-$C_{12}$ alkyl is optionally substituted with a group —$OR^5$;
$R^4$ is $C_1$-$C_{12}$-alkyl;
$R^5$ is hydrogen;
$R^6$ is $C_1$-$C_{12}$-alkyl;

or a diastereoisomer, enantiomer, tautomer or salt thereof.

27. A compound as claimed in claim 1, selected from the group consisting of:
4-hydroxy-4-methyl-piperidine-1-carboxylic acid (4-{[2-(2-methyl-2H-indazol-6-ylcarbamoyl)-phenylamino]-methyl}-pyridin-2-yl)-amide,
4-hydroxy-piperidine-1-carboxylic acid (4-{[2-(2-methyl-2H-indazol-6-ylcarbamoyl)-phenylamino]-methyl}-pyridin-2-yl)-amide,
4-hydroxy-4-trifluoromethyl-piperidine-1-carboxylic acid (4-{[2-(2-methyl-2H-indazol-6-ylcarbamoyl)-phenylamino]-methyl}-pyridin-2-yl)-amide,
1-oxo-thiomorpholine-4-carboxylic acid (4-{[2-(2-methyl-2H-indazol-6-ylcarbamoyl)-phenylamino]-methyl}-pyridin-2-yl)-amide,
1,1-dioxo-thiomorpholine-4-carboxylic acid (4-{[2-(2-methyl-2H-indazol-6-ylcarbamoyl)-phenylamino]-methyl}-pyridin-2-yl)-amide,
4-methyl-piperazine-1-carboxylic acid (4-{[2-(2-methyl-2H-indazol-6-ylcarbamoyl)-phenylamino]-methyl}-pyridin-2-yl)-amide,
4-methyl-piperazine-1-carboxylic acid (4-{[2-(1-methyl-1H-indazol-6-ylcarbamoyl)-phenylamino]-methyl}-pyridin-2-yl)-amide,
4-(2-hydroxy-ethyl)-piperazine-1-carboxylic acid (4-{[2-(1-methyl-1H-indazol-6-ylcarbamoyl)-phenylamino]-methyl}-pyridin-2-yl)-amide,
4-(2-hydroxy-ethyl)-piperazine-1-carboxylic acid (4-{[2-(2-methyl-2H-indazol-6-ylcarbamoyl)-phenylamino]-methyl}-pyridin-2-yl)-amide,
4-methanesulfonyl-piperazine-1-carboxylic acid (4-{[2-(2-methyl-2H-indazol-6-ylcarbamoyl)-phenylamino]-methyl}-pyridin-2-yl)-amide,
morpholine-4-carboxylic acid (4-{[2-(1-methyl-1H-indazol-6-ylcarbamoyl)-phenylamino]-methyl}-pyridin-2-yl)-amide,
morpholine-4-carboxylic acid (4-{[2-(2-methyl-2H-indazol-6-ylcarbamoyl)-phenylamino]-methyl}-pyridin-2-yl)-amide,
morpholine-4-carboxylic acid (4-{[2-(7-methoxy-isoquinolin-3-ylcarbamoyl)-phenylamino]-methyl}-pyridin-2-yl)-amide,
2,6-dimethyl-morpholine-4-carboxylic acid (4-{[2-(1-methyl-1H-indazol-6-ylcarbamoyl)-phenylamino]-methyl}-pyridin-2-yl)-amide,
2,6-dimethyl-morpholine-4-carboxylic acid (4-{[2-(2-methyl-2H-indazol-6-ylcarbamoyl)-phenylamino]-methyl}-pyridin-2-yl)-amide,
3-hydroxy-pyrrolidine-1-carboxylic acid (4-{[2-(2-methyl-2H-indazol-6-ylcarbamoyl)-phenylamino]-methyl}-pyridin-2-yl)-amide,
morpholine-4-carboxylic acid (4-{[3-fluoro-2-(2-methyl-2H-indazol-6-ylcarbamoyl)-phenylamino]-methyl}-pyridin-2-yl)-amide,
morpholine-4-carboxylic acid (4-{[2-(isoquinolin-3-ylcarbamoyl)-phenylamino]-methyl}-pyridin-2-yl)-amide,
morpholine-4-carboxylic acid (4-{[2-(3,6-difluoro-quinolin-2-ylcarbamoyl)-phenylamino]-methyl}-pyridin-2-yl)-amide, and
morpholine-4-carboxylic acid (4-{[2-(3-fluoro-6-methoxy-quinolin-2-yl carbamoyl)-phenylamino]-methyl}-pyridin-2-yl)-amide, and a diastereoisomer, enantiomer, tautomer and salt thereof.

28. A pharmaceutical composition, comprising at least one compound of formula (I) according to claim 1 and a pharmaceutically acceptable carrier.

29. A pharmaceutical composition, comprising at least one compound of formula (I) according to claim 27 and at least one pharmaceutically acceptable carrier.

30. A method for treating a disease associated with persistent angiogenesis or a disease associated with excessive lymphangiogenesis, comprising administering to a subject in need thereof an effective amount of a pharmaceutical composition according to claim 28.

31. A method for inhibiting VEGF receptor kinase 3 lymphangiogenesis, comprising administering to a subject in need thereof an effective amount of a pharmaceutical composition according to claim 28.

32. A method inhibition of angiogenesis and/or lymphangiogenesis and/or the VEGF receptor kinases, comprising administering to a subject in need thereof an effective amount of a pharmaceutical composition according to claim 28.

33. A method for inhibiting the tyrosine kinases VEGFR-1 or VEGFR-2, comprising administering to a subject in need thereof an effective amount of a pharmaceutical composition according to claim 28.

34. A compound of formula (III):

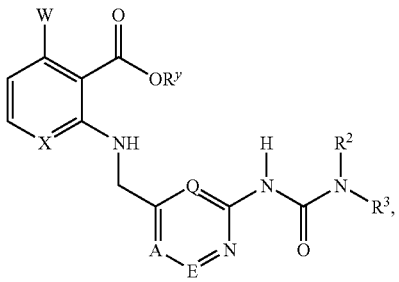

in which
X is CH;
W is hydrogen or fluorine;
A, E and Q independently of one another, are CH or N, wherein only a maximum of two nitrogen atoms are contained in the ring;
$R^2$ and $R^3$ together with the nitrogen atom to which they are attached form a 3-8 membered heterocycloalkyl ring, which optionally contains at least one further heteroatom and which is optionally substituted in one or more places in the same way or differently with halogen, cyano, $C_1$-$C_{12}$-alkyl, $C_1$-$C_{12}$-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, wherein $C_1$-$C_{12}$ alkyl is optionally substituted with a group —$OR^5$;
$R^4$ is $C_1$-$C_{12}$-alkyl, $C_3$-$C_8$-cycloalkyl, aryl or heteroaryl;
$R^5$ is hydrogen, $C_1$-$C_{12}$-alkyl, $C_3$-$C_8$-cycloalkyl or halo-$C_1$-$C_6$-alkyl;
$R^6$ is hydrogen, $C_1$-$C_{12}$-alkyl, $C_3$-$C_8$-cycloalkyl, halo-$C_1$-$C_6$-alkyl, aryl or —$NR^7R^8$;
$R^7$ and $R^8$ independently of one another, are hydrogen, —$SO_2R^6$, —$COR^6$, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —$OR^5$ or —$N(CH_3)_2$, or
$R^7$ and $R^8$ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —$OR^5$, —$COR^6$, —$SR^4$, —$SOR^4$ or —$SO_2R^6$; and
$R^y$ is H or $C_1$-$C_6$-alkyl.

35. A compound as claimed in claim 34, wherein $R^y$ is H or $C_1$-$C_2$-alkyl.

36. A process for preparing a compound of formula (I) according to claim 1, comprising
reacting a compound of formula (III):

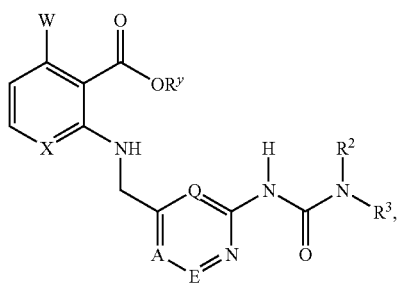

in which A, E, Q, W, X, $R^2$ and $R^3$, are defined as for the compound of formula (I), and $R^y$ is H or $C_1$-$C_6$-alkyl,
with an amine of formula $R^1NH_2$, in which $R^1$ is defined as for the compound of formula (I).

37. A process for preparing a compound of formula (I) according to claim 1, comprising a compound of formula (II):

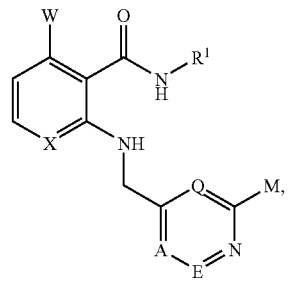

wherein A, E, Q, W, X, and $R^1$ are defined as for the compound of formula (I), and M stands for halogen, is:
(i) first converted to an amine and subsequently converted to a compound of formula (I) by reaction with a carbamoyl chloride of formula $ClCONR^2R^3$, wherein $R^2$ and $R_3$ are defined as for the compound of formula (I);
or alternatively,
(ii) reacted with a compound of formula $H_2NCONR^2R^3$, wherein $R^2$ and $R^3$ are defined as for the compound of formula (I);
or alternatively,
(iii) first converted to an amine, then converted to a compound of formula (I) by first reacting with a compound of formula $ClCO_2Ph$ and then reacting with a compound of formula $HNR^2R^3$, wherein $R^2$ and $R^3$ are defined as for the compound of formula (I).

38. A process as claimed in claim 37, wherein the compound of formula (II) is reacted with a compound of formula $H_2NCONR^2R^3$.

39. A compound of formula (I) according to claim 1, wherein:
W is hydrogen or fluorine;
A, E and Q independently of one another, are CH or N, wherein only a maximum of two nitrogen atoms are contained in the ring;
$R^1$ is aryl or heteroaryl, which is optionally substituted in one or more places in the same way or differently with halogen, hydroxy, $C_1$-$C_{12}$-alkyl, $C_2$-$C_6$-alkenyl, $C_1$-$C_{12}$-alkoxy, halo-$C_1$-$C_6$-alkyl, =O, —$SO_2R^6$, —$OR^5$, —$SOR^4$, —$COR^6$, —$CO_2R^6$ or —$NR^7R^8$, wherein $C_1$-$C_{12}$-alkyl may be substituted with —$NR^7R^8$;
$R^2$ and $R^3$ together with the nitrogen atom to which they are attached form a 3-8 membered heterocycloalkyl ring, which optionally contains at least one further heteroatom and which is optionally substituted in one or more places in the same way or differently with halogen, cyano, $C_1$-$C_{12}$-alkyl, $C_1$-C12-alkoxy, halo-$C_1$-$C_6$-alkyl, $C_1$-$C_3$-dialkyl ketal, $C_1$-$C_3$-cyclic ketal, =O, —$OR^5$, —$SR^4$, —$SOR^4$, —$SO_2R^6$, —$COR^6$ or —$CO_2R^6$, wherein $C_1$-$C_{12}$ alkyl is optionally substituted with a group —$OR^5$;
$R^4$ is $C_1$-$C_{12}$-alkyl, $C_3$-$C_8$-cycloalkyl, aryl or heteroaryl;
$R^5$ is hydrogen, $C_1$-$C_{12}$-alkyl, $C_3$-$C_8$-cycloalkyl or halo-$C_1$-$C_6$-alkyl;
$R^6$ is hydrogen, $C_1$-$C_{12}$-alkyl, $C_3$-$C_8$-cycloalkyl, halo-$C_1$-$C_6$-alkyl, aryl or —$NR^7R^8$;

R⁷ and R⁸ independently of one another, are hydrogen, —SO₂R⁶, —COR⁶, aryl, $C_3$-$C_8$-cycloalkyl, $C_1$-$C_{12}$-alkyl, halo-$C_1$-$C_{12}$-alkyl or $C_1$-$C_{12}$-alkoxy, wherein $C_1$-$C_{12}$-alkyl is optionally substituted with —OR⁵ or —N(CH₃)₂, or R⁷ and R⁸ provide a 3-8 membered cycloalkyl ring, which optionally contains at least one further heteroatom and is optionally substituted in one or more places in the same way or differently with halogen, cyano, $C_1$-$C_{12}$-alkyl, $C_1$-$C_{12}$-alkoxy, halo-$C_1$-$C_6$-alkyl, =O, —OR⁵, —COR⁶, —SR⁴, —SOR⁴ or —SO₂R⁶;

or a salt thereof.

40. A compound as claimed in claim 1, selected from the group consisting of:

4-hydroxy-4-methyl-piperidine-1-carboxylic acid (4-{[2-(2-methyl-2H-indazol-6-ylcarbamoyl)-phenylamino]-methyl}-pyridin-2-yl)-amide, 4-hydroxy-piperidine-1-carboxylic acid (4-{[2-(2-methyl-2H-indazol-6-ylcarbamoyl)-phenylamino]-methyl}-pyridin-2-yl)-amide, 4-hydroxy-4-trifluoromethyl-piperidine-1-carboxylic acid (4-{[2-(2-methyl-2H-indazol-6-ylcarbamoyl)-phenylamino]-methyl}-pyridin-2-yl)-amide, 1-oxo-thiomorpholine-4-carboxylic acid (4-{[2-(2-methyl-2H-indazol-6-ylcarbamoyl)-phenylamino]-methyl}-pyridin-2-yl)-amide, 1,1-dioxo-thiomorpholine-4-carboxylic acid (4-{[2-(2-methyl-2H-indazol-6-ylcarbamoyl)-phenylamino]-methyl}-pyridin-2-yl)-amide, 4-methyl-piperazine-1-carboxylic acid (4-{[2-(2-methyl-2H-indazol-6-ylcarbamoyl)-phenylamino]-methyl}-pyridin-2-yl)-amide, 4-methyl-piperazine-1-carboxylic acid (4-{[2-(1-methyl-1H-indazol-6-ylcarbamoyl)-phenylamino]-methyl}-pyridin-2-yl)-amide, 4-(2-hydroxy-ethyl)-piperazine-1-carboxylic acid (4-{[2-(1-methyl-1H-indazol-6-ylcarbamoyl)-phenylamino]-methyl}-pyridin-2-yl)-amide, 4-(2-hydroxy-ethyl)-piperazine-1-carboxylic acid (4-{[2-(2-methyl-2H-indazol-6-ylcarbamoyl)-phenylamino]-methyl}-pyridin-2-yl)-amide, 4-methanesulfonyl-piperazine-1-carboxylic acid (4-{[2-(2-methyl-2H-indazol-6-ylcarbamoyl)-phenylamino]-methyl}-pyridin-2-yl)-amide, morpholine-4-carboxylic acid (4-{[2-(1-methyl-1H-indazol-6-ylcarbamoyl)-phenylamino]-methyl}-pyridin-2-yl)-amide, morpholine-4-carboxylic acid (4-{[2-(2-methyl-2H-indazol-6-ylcarbamoyl)-phenylamino]-methyl}-pyridin-2-yl)-amide, morpholine-4-carboxylic acid (4-{[2-(7-methoxy-isoquinolin-3-ylcarbamoyl)-phenylamino]-methyl}-pyridin-2-yl)-amide, 2,6-dimethyl-morpholine-4-carboxylic acid (4-{[2-(1-methyl-1H-indazol-6-ylcarbamoyl)-phenylamino]-methyl}-pyridin-2-yl)-amide, 2,6-dimethyl-morpholine-4-carboxylic acid (4-{[2-(2-methyl-2H-indazol-6-ylcarbamoyl)-phenylamino]-methyl}-pyridin-2-yl)-amide, 3-hydroxy-pyrrolidine-1-carboxylic acid (4-{[2-(2-methyl-2H-indazol-6-ylcarbamoyl)-phenylamino]-methyl}-pyridin-2-yl)-amide, morpholine-4-carboxylic acid (4-{[3-fluoro-2-(2-methyl-2H-indazol-6-ylcarbamoyl)-phenylamino]-methyl}-pyridin-2-yl)-amide, morpholine-4-carboxylic acid (4-{[2-(isoquinolin-3-ylcarbamoyl)-phenylamino]-methyl}-pyridin-2-yl)-amide, morpholine-4-carboxylic acid (4-{[2-(3,6-difluoro-quinolin-2-ylcarbamoyl)-phenylamino]-methyl}-pyridin-2-yl)-amide, and morpholine-4-carboxylic acid (4-{[2-(3-fluoro-6-methoxy-quinolin-2-yl carbamoyl)-phenylamino]-methyl}-pyridin-2-yl)-amide, and a pharmaceutically acceptable salt thereof.

\* \* \* \* \*

UNITED STATES PATENT AND TRADEMARK OFFICE
CERTIFICATE OF CORRECTION

PATENT NO.       : 7,572,794 B2                              Page 1 of 1
APPLICATION NO. : 11/265516
DATED            : August 11, 2009
INVENTOR(S)      : Bohlmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 847 days.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,572,794 B2  
APPLICATION NO. : 11/265516  
DATED : August 11, 2009  
INVENTOR(S) : Bohlmann et al.

Page 1 of 1

It is certified that error appears in the above-identified patent and that said Letters Patent is hereby corrected as shown below:

Column 42, line 64 reads "$C_1$-$C_3$-dialkyl ketal, $C_1$-$C_3$-cyclic ketal, =O, -$OR^5$," should read -- $C_1$-$C_3$-dialkyl ketal, $C_1$-$C_3$-cyclic ketal, =O, -$OR^5$, $SR^4$ --

Column 46, line 24 reads "oyl chloride of formula $ClCONR^2R^3$, wherein $R^2$ and $R_3$" should read -- oyl chloride of formula $ClCONR^2R^3$, wherein $R^2$ and $R^3$ --

Signed and Sealed this  
Eighth Day of March, 2011

David J. Kappos  
*Director of the United States Patent and Trademark Office*